US005902794A

United States Patent [19]
Cho-Chung

[11] Patent Number: 5,902,794
[45] Date of Patent: May 11, 1999

[54] 8-CI CAMP AS ANTI-CANCER DRUG

[75] Inventor: Yoon Sang Cho-Chung, Bethesda, Md.

[73] Assignee: The United States of America as represented by the Secretary of the Department of Health and Human Services, Washington, D.C.

[21] Appl. No.: 08/937,020

[22] Filed: Sep. 24, 1997

Related U.S. Application Data

[63] Continuation of application No. 08/329,764, Oct. 27, 1994, Pat. No. 5,792,752, which is a continuation of application No. 07/896,452, Jun. 4, 1992, abandoned, which is a continuation of application No. 07/198,489, May 23, 1988, abandoned.

[51] Int. Cl.$^6$ .......................... A61K 31/70; C07H 19/213
[52] U.S. Cl. .......................................... 514/47; 536/26.13
[58] Field of Search ............................. 514/47; 536/26.13

[56] References Cited

U.S. PATENT DOCUMENTS

| | | | |
|---|---|---|---|
| 3,849,397 | 11/1974 | Robins et al. | 536/26.13 |
| 3,849,553 | 11/1974 | Dea et al. | 514/47 |
| 3,856,776 | 12/1974 | Cehovic et al. | 536/26.13 |
| 3,948,886 | 4/1976 | Shuman et al. | 536/26.12 |
| 4,058,659 | 11/1977 | Robins et al. | 536/26.12 |
| 4,208,406 | 6/1980 | Lapinet et al. | 514/47 |
| 4,369,181 | 1/1983 | Miller et al. | 514/47 |
| 4,861,873 | 8/1989 | Robins et al. | 536/26.13 |
| 5,026,836 | 6/1991 | Robins et al. | 536/26.12 |
| 5,041,426 | 8/1991 | Robins et al. | 514/43 |

FOREIGN PATENT DOCUMENTS

WO 89/05647   5/1989   WIPO .

OTHER PUBLICATIONS

Y. S. Cho–Chung, "Site Selective 8–Chloro–Cyclic Adenosine 3', 5'–Monophosphate as a Biologic Modulator of Cancer: Restoration of Normal Control Mechanisms," *J. Nat. Cancer Inst. USA*, 81(13), 982–987 (Jul. 5, 1989).
Katsaros et al., "Site–Selective Cyclic AMP Analogs Provide a New Approach Control of Cancer Cell Growth," *FEBS Letters*, 223(1), 97–103 (Oct., 1987).
Cho–Chung et al.(I), "Site Selective cAMP Analogs are Cytostatic and Differentiating Agents for a Spectrum of Human Cancer Cell Lines: Potential for Application to Chemotherapy," *Proc. Am. Soc. Clin. Oncology*, 6, Abstr. 62, p. 17, (Mar. 17, 1987).
Cho–Chung et al. (II), "In vivo Inhibition of Growth of Two Hormone–Dependent Mammary Tumors by Dibutyryl Cyclic AMP," *Science*, 183, 87–88 (Jan. 11, 1974).
Tagliaferri et al.(I), "Reverse Transformation of Harvey Murine Sarcoma Virus–transformed NIH/3T3 Cells by Site–Selective Cyclic AMP Analogs," *J. Biol. Chem.*, 263(1), 409–416 (Jan. 5, 1988).

Tagliaferri et al.(II), "Synergistic Inhibition of Growth of Breast and Colon Human Cancer Cell Lines by Site–Selective Cyclic AMP Analogues," *Cancer Res.*, 48, 1642–1650 (Mar. 15, 1988).
Tortora et al., "Site–Selective cAMP Analogs at Micromolar Concentrations Induce Growth Arrest and Differentiation of Acute Promyelocytic, Chronic Myelocytic, and Acute Lymphocytic Human Leukemia Cell Lines," *Blood*, 71(1), 230–233 (Jan., 1988).
Niles et al., "Regulation of Phosphatidylcholine Metabolism By Cyclic AMP in a Model Alveolar Type 2 Cell Line," *J. Biol. Chem.*, 254(11), 4324–4326 (Jun. 10, 1979).
Miller et al., "Synthesis and Enzymatic and Inotropic Activity of Some New 8–Substituted and 6,8–Disubstituted Derivatives of Adenosine Cyclic 3', 5'–Monophosphate," *J. Med. Chem.*, 23(3), 242–251 (1980).
Mineyama et al., "Synthesis and Biological Activity of 8–Haloadenosine 3', 5'–Cyclic Phosphates," *J. Carbohydrates Nucleosides Nucleotides*, 1(1), 55–60 (1974).
Tsuji et al., "Neuronal Differentiation of Oat Cell Carcinoma In Vitro by Dibutyryl Cyclic Adenosine 3',5'–Monophosphate," *Cancer Letters*, 1, 311–318 (1976).
Helson et al., "A Rationale for the Treatment of Metastatic Neuroblastoma," *J. Nat. Cancer Inst. USA*, 57(3), 727–729 (Sep., 1976).
Holmgren et al., "In Vivo Modulation of Intracellular cAMP and Cell Growth of a Lymphatic Tumour in Mice by Cholera Toxin," *Experimental Cell Res.*, 108, 31–39 (1977).
Prasad, "Differentiation of Neuroblastoma Cells in Culture," *Biology Rev.*, 50, 129–165 (1975).
Rannels et al., "Two Different Intrachain cAMP Binding Sites of cAMP–dependent Protein Kinases," *J. Biol. Chem.*, 255(15), 7085–7088 (Aug. 10, 1980).
Ogreid et al., "Activation of Protein Kinase Isozymes by Cyclic Nucleoside Analogs Used Singly or in Combination," *Eur. J. Biochem*, 150, 219–227 (1985).
Robinson–Steiner et al., "Probable Involvement of Both Intrachain cAMP Binding Sites in Activation of Protein Kinase," *J. Biol. Chem.*, 258(2), 1032–1040 (Jan. 25, 1983).
T. Beardsley, "Trends in Cancer Epidemiology—A War Not Won," *Scientific American*, 270(1), 130–138 (Jan., 1994).
Tortora et al., "Phase I Clinical Study with 8–Chloro–cAMP and Evaluation of Immunological Effects in Cancer Patients," *Clinical Cancer Research*, 1, 377–384 (Apr., 1995).

*Primary Examiner*—Marian C. Knode
*Assistant Examiner*—L. Eric Crane
*Attorney, Agent, or Firm*—Leydig, Voit & Mayer, Ltd.

[57] ABSTRACT

Site 1- and site 2-selective derivatives of cAMP have been found to inhibit the of a variety of cancer and leukemic cells. The compounds have been found to have a synergistic effect in cancer and leukemic cell growth inhibition when a site 1-selective compounds is used in combination with a site 2-selective compound.

16 Claims, 10 Drawing Sheets

FIG. 2E
FIG. 2F
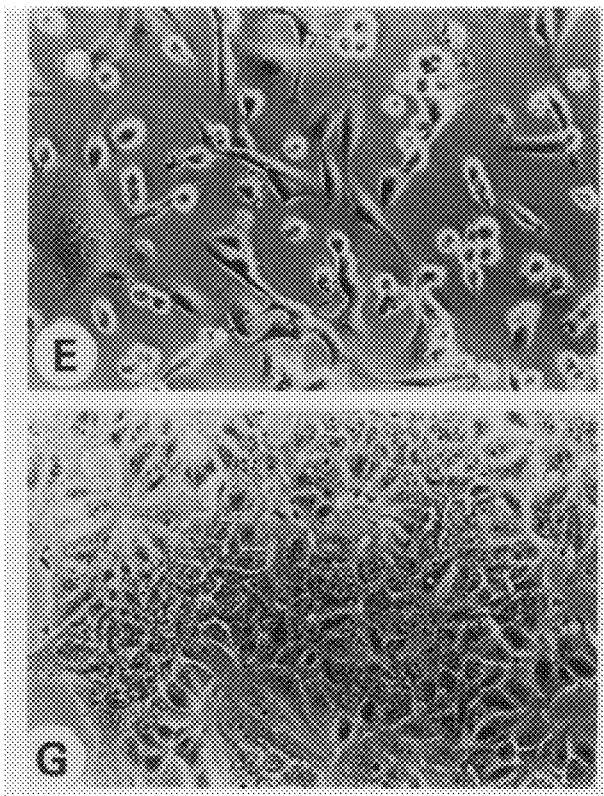
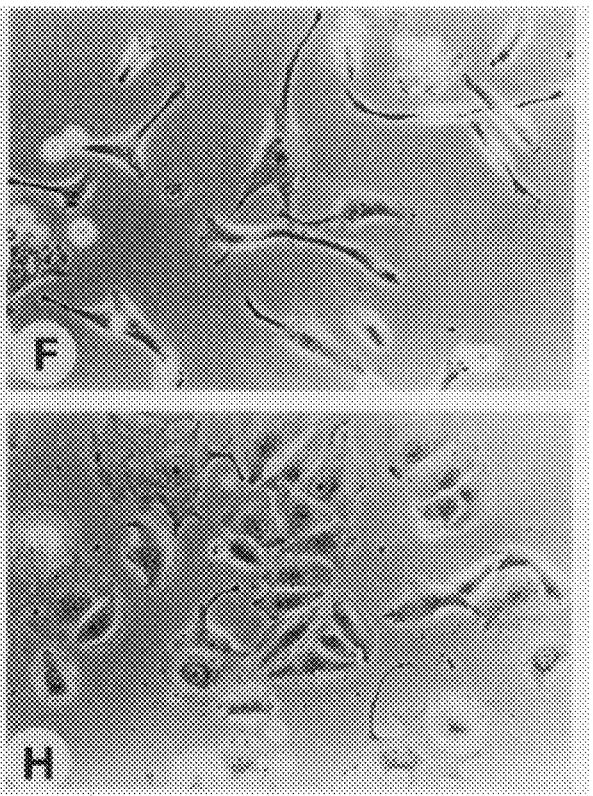
FIG. 2G
FIG. 2H

# 8-Cl CAMP AS ANTI-CANCER DRUG

This application is a continuation of U.S. patent application Ser. No. 08/329,764 filed on Oct. 27, 1994, now U.S. Pat. No. 5,792,752, which is a continuation of U.S. patent application Ser. No. 07/896,452, filed on Jun. 4, 1992, now abandoned, which is a continuation of U.S. patent application Ser. No. 07/198,489, filed May 23, 1988, now abandoned.

FIELD OF THE INVENTION

The present invention relates to improvements in cancer chemotherapy; and, more particularly, to a composition and method for use in cancer therapy based on cyclic AMP derivatives.

BACKGROUND OF THE INVENTION

Cyclic adenosine monophosphate (cAMP) is a naturally occurring compound that is present in all cells and tissues, from bacteria to humans. In animal cells, cAMP appears to promote the expression of differentiated (specialized) properties. Well-known examples are the stimulation by cAMP of gluconeogenesis in liver, lipolysis in fat tissues, and water permeability in toad bladder epithelium. The functional development of the mammary gland is another example. The content of cAMP in rat mammary gland shows a diphasic pattern during the gestation cycle. The level of cAMP rises continuously toward the end of pregnancy, and then falls progressively to its lowest value by the 16th day of lactation. The transition at the time of parturition coincides with a considerable increase in the metabolic activity of the gland consequent to the onset of lactation.

Morphological alterations induced by cAMP in cultured cells in vitro include acinar formation and ultrastructural changes in thyroid cells, elongation and array formation in fibroblasts, development of neurite-like outgrowths in neuroblastoma cells, growth of processes in glioma cells, and pigmentation of melanocytes. The rapid changes in cell morphology are probably mediated through an effect by cAMP in interaction with $Ca^{2+}$ on the cytoskeleton. Among the functional effects of cAMP are induction of specific enzymes stimulation of collagen synthesis in fibroblasts, and neurotransmitter synthesis in cells of neural origin. It is significant that cAMP-induced differentiation may occur without concomitant inhibition of cell division.

While a role for cAMP in cell differentiation seems to be established, it is much more difficult to define a general function for this nucleotide in the regulation of cell proliferation. The available data are interpreted very differently.

In fibroblasts, a number of studies have shown that treatment, which relieves growth inhibition in quiescent cells, such as serum addition or trypsinization, leads to decreased adenylate cyclase activity and a rapid fall in cAMP before the onset of DNA synthesis, supporting the idea that a drop in cAMP level is the decisive signal triggering cell division. However, conclusive evidence that the reduction in cAMP is causally related to the initial release from the resting state has not been presented. In cultured human fibroblasts, when DBcAMP or methylisobutylxanthine was added to prevent the cAMP drop during the first eight hours after serum addition, subsequent DNA synthesis was not delayed, whereas these agents were inhibitory when added more than eight hours after serum addition, in mid G1, and in late G1 and S phases of the cell cycle. This indicates that a reduction in cAMP may not be involved as the initial trigger for serum-stimulated DNA synthesis, but it may be a factor at later stages, necessary for further progression toward DNA replication. However, in Balb/3T3 cells ($Ca^{2+}$ deprived) stimulated by serum, there is an increase in cAMP in late G1, suggesting a positive role for cAMP in the control of DNA replication in fibroblasts.

Apparent contradictory data also exist in the study of lymphocytes. Cyclic AMP in low concentrations ($10^{-8}$ to $10^{-6}$M) triggers DNA) synthesis in suspension cultures of rat thymic lymphocytes, providing one of the main arguments for a growth-promoting role of cAMP. Experiments on peripheral lymphocytes have yielded data that partly support and partly conflict with these results. For liver cells, there is increasing evidence that cAMP may have a positive effect on growth.

Studies showing growth inhibition by cAMP have tended to use higher concentrations of DBcAMP or the other agents than those studies showing growth stimulation, possibly indicating that the growth inhibitory effects seen are less physiological. It has become increasingly evident that effects seen after addition to biological systems of high concentrations of cAMP or DBcAMP are not necessarily direct effects of cAMP, but may be caused by metabolites, such as 5'AMP, adenosine, or butyrate. Similarly, methylxanthines have effects that probably are not mediated through cAMP. Physiologically, it seems that cAMP has several intracycle modulatory effects on normal cell growth, although it is quite certainly not the single growth regulator. Probably various growth factors operate by mechanisms independent of cAMP. In fact, cAMP may not be essential for cell cycle progression per se.

The effect of cAMP observed in malignant cells in culture in many cases constitutes a striking redifferentiation, which amounts to apparent renormalization of a number of properties of the transformed cells, including morphological features, adhesive properties, lectin agglutination, cell movement, biochemical functions, and anchorage-dependent growth.

It is unclear how fundamental this "normalization" is. For example, the tumorigenicity of DBcAMP-treated neuroblastoma cells has been reported to be decreased by Prasad (*Biol. Rev.* 50: 129–165, 1975), but was found to be unaltered in another study by Furmanski et al. (J. Schultz, and H. G. Gratzner, Eds., *The Role of Cyclic Nucleotides in Carcinogenesis*, pp. 239–261). New York and London: Academic Press, 1973. The presence of transformation-associated antigens on the cell surface is not prevented by cAMP. There is considerable variation in the morphological response to cAMP from cell to cell, even among fibroblasts.

Animal experiments have shown that various cAMP derivatives may inhibit: tumor growth in vivo (cf. Keller, *Life Sci.* 11: 485–491, 1972, and Cho-Chung et al., *Science* 183: 87–88, 1974). An interesting observation was that one single injection of cholera toxin, which is a potent adenylate cyclase activator, caused an almost complete inhibition of YAC lymphoma cell proliferation for up to four days in mice without noticeable toxic effects on the animals (Holmgren et al., *Exp. Cell Res.* 108: 31–39, 1977). Some of the most striking examples of malignant cell differentiation by cAMP in vitro have been observed in neuroblastoma cultures (Prasad, *Biol. Rev.* 50: 129–165, 1975).

A preliminary clinical study with the phosphodiesterase inhibitor papaverine, included in a combined drug regimen for disseminated neuroblastomas that in most cases were unresponsive to other drugs, has yielded promising results (Helson et al., *J. Natl. Cancer Inst.* 57: 727–729; 1976). Also, human oat cell lung carcinoma cells treated in vitro with DBcAMP have differentiated into neurone-like cells (Tsuji et al., Cancer Lett. 1: 311–318, 1976). Another interesting example is the induction of differentiation by DBcAMP of spindle cell sarcoma with multiple metastasis (Williams et al., Proc. Am. Assoc. Cancer Res. 23: 142, 1983). In this latter case, the patient was treated with DBcAMP (3–6 mg/kg) intravenously daily over five hours on days 1–9 and again on days 47–56. The tumor size plateaued and even decreased during both infusion periods and increased during intervals off treatment and after cessation of the second treatment. Histology of tumors biopsied on days 2, 14, and 60 showed evidence of differentiation during the DBcAMP infusion.

Because cAMP manifests almost ubiquitous biological effects, the unphysiologically high levels of cellular AMP that would result from prior compounds would disturb many cellular processes nonspecifically, resulting in a masking of a specific function of cAMP, such as growth regulation.

Cyclic AMP in mammalian cells functions via binding to its receptor protein, the regulatory subunit of cAMP-dependent protein kinase. There are at least two distinct isozymes for cAMP-dependent protein kinase, namely, type I and type II protein kinases, having different regulatory subunits but an identical catalytic subunit, and differential expression of these isozymes has been shown to be linked to regulation of cell growth and differentiation. Recently, two genes have been identified that code for two different catalytic subunits (C$\alpha$, C$\beta$) of cAMP-dependent protein kinase. However, preferential coexpression of either one of these catalytic subunits with either the type I or the type II regulatory subunit has not been found.

Because a mixture of type I and type II kinase isozymes is present in most tissues, selective modulation of these isozymes in intact cells may be a crucial function of cAMP. All past studies of the cAMP regulation of cell growth employed either a few early known cAMP analogues that require an effective concentration of unphysiologically high millimolar range or agents that raise cellular cAMP to abnormally and continuously high levels. Under these experimental conditions, separate modulation of type I and type II kinase isozymes is not possible, because cAMP at high levels activates both isozymes maximally and equally without discrimination.

Recent studies on extensive cAMP binding kinetics, using purified preparations of protein kinase isozymes in vitro, identified site-selective cAMP analogs that selectively bind to either one of two different binding sites on the cAMP receptor protein. Furthermore, the site-selective analogues in appropriate combinations demonstrate synergism of binding and exhibit specificity toward either type I or type II protein kinase. This unique site-specificity of site-selective cAMP analogues is not mimicked by cAMP itself or by previously studied earlier analogues.

Human breast cancers often regress after hormone therapy, treatment that frequently involves the removal of the ovaries. The cancer regression has been linked to the presence of an ER in the tumor, to the extent that assays designed to measure the receptor are now used extensively to identify patients likely to respond to hormone therapy. However, it has become apparent that the mere presence of ER is not a reliable criterion for the response of mammary tumors to endocrine therapy. While patients with undetectable levels of tumor ER rarely respond to endocrine therapy, only 50–60% of ER-positive human breast tumors regress after hormone treatment. There is, therefore, a need to identify hormone-dependent cancers within the group of ER-positive tumors. The presence of PgR in ER-positive tumors has been reported to improve the prediction of endocrine responsiveness in some studies, but in other studies, PgR did not enhance prediction. The presence of PgR, therefore, does not necessarily improve the predictive value of ER. Additional discriminating factors are clearly required.

Evidence that cAMP receptor protein may represent such a parameter has come from studies in which regression of hormone-dependent mammary tumors followed administration of dibutyryl cyclic AMP, the effect being apparently mediated by cAMP receptor protein. Cyclic AMP receptor protein appears to be a marker of tumor sensitivity to hormonal manipulation as was shown in animal tumors and in a limited number of human breast cancers.

It has been suggested that regulation of the growth of hormone-dependent mammary tumors may depend on the antagonistic action between estrogen and cyclic AMP. Estrogen stimulates, whereas cAMP arrests, the growth of mammary carcinomas induced by 7,12-dimethyl-benz($\alpha$) anthracene (DMBA) in the rat. During growth arrest of the tumors, after either hormone removal via ovariectomy or treatment of the hosts with $N^6,O^{2'}$-dibutyryl-cAMP (DBcAMP), estrogen binding decreases; whereas cAMP binding and cAMP-dependent protein kinase activity increase in the cytosol and nuclei of the tumor cells. It was further demonstrated that the growth of DMBA-induced mammary tumors is associated with an enhanced expression of a cellular oncogene, c-ras. The p21 transforming protein of the ras gene product was a predominant in vitro translation product of mRNAs of the growing tumors, and a sharp reduction of the translated p21 protein preceded regression of these tumors after either ovariectomy or DBcAMP treatment.

Recent studies on cAMP binding kinetics, using purified preparations of cAMP-dependent protein kinases, identified cAMP analogues that are potent activators of protein kinase and selectively bind to either one of the two different cAMP binding sites of protein kinase (cf. Rannels et al. J. Biol. Chem. 255: 7085–7088, 1980). Generally, analogues modified at the C-8 position of the adenine ring are site 1-selective, and those modified at the C-6 position are site 2-selective. Furthermore, the Site 1- and Site 2-selective analogues in combination demonstrate synergism of binding to and activation of protein kinase, (Robinson-Steiner et al., J. Biol. Chem. 258: 1032–1040, 1983).

SUMMARY OF THE INVENTION

It is an object of the present invention to overcome deficiencies in the prior art.

It is a further object to provide improvements in cancer and leukemia chemotherapy.

It is another object of the present invention to provide compounds which are useful in cancer and leukemia chemotherapy.

It is yet a further object of the present invention to provide synergistic combinations of compounds that are useful in cancer and leukemia chemotherapy.

It is still a further object to provide an improved anticancer therapeutic method.

It is yet another object of the present invention to provide an improved chemotherapy regimen for treating leukemia.

According to the present invention, site-selective cAMP analogues, which are manyfold more active in binding to the cAMP receptor protein than previously studied analogues, demonstrate a potent growth inhibition of a great number of human cancer cell lines.

The cAMP receptor protein has two different cAMP binding sites, and cAMP analogues that selectively bind to either one of the two binding sites are known as either site 1-selective (C-8 analogues) or site 2-selective (C-6 analogues).

The three most potent compounds so far noted among the group are the 8-Cl, the $N^6$-benzyl, and the $N^6$-phenyl-8-p-chlorophenylthio-analogues of cAMP.

The C-6 analogues, used in combination with halogen or thio derivatives of the C-8 analogues, demonstrate synergistic enhancement of growth inhibition. The growth inhibition parallels a change in cell morphology, an augmentation of the $R^{II}$ cAMP receptor protein, and a reduction in p21 ras protein.

The site-selective cAMP analogues of the present invention provide a new physiological means to control the growth of a variety of human cancer cells.

In this Figure, the values of $IC_{50}$ (concentration inducing 50% inhibition of cell proliferation) were obtained in reference to the growth of untreated control cells. In the chart, 1 is MCF-7, 2 is T-47D, 3 is ZR-75-1, 4 is MCF-7ras-, 5 is MDA-MB-231, 6 is BT-20, 7 is HBL-100, 8 is LS-174T, 9 is WiDr, and 10 is HT-29.

FIG. 2 shows the effect of cAMP analogues on the morphology of breast cancer cell lines A and B, T-47D, C and D, HBL-100; E and F, MDA-MB-231; G and H, MCF-7ras; B, D, F, and H, treatment with 8-Cl-cAMP at 50 microM at Day 0 and Day 2; and A, C, E, and G, untreated control cells. The photographs were taken on Day 4, ×160.

Figure 3:
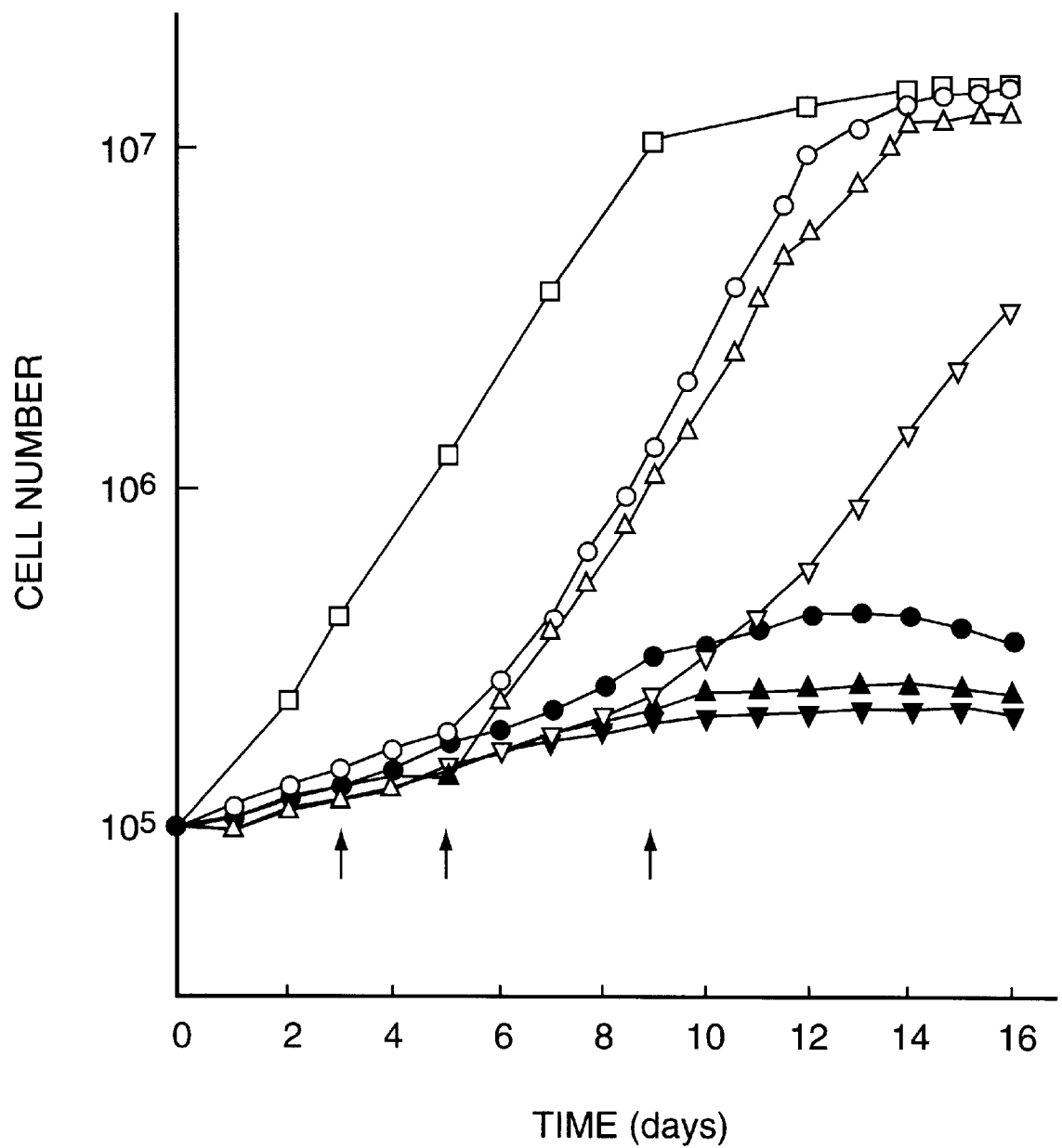

FIG. 3 shows a comparison of the effect of 8-Cl-cAMP and 8-Cl-adenosine on the growth of LS-174T colon cancer line. □, untreated control cell; ○, Δ, ∇, cells treated with 8-Cl-cAMP (10 microM) for 3, 6, and 9 days, respectively; and ●, ▲, ▼, cells treated with 8-Cl-adenosine (5 microM) for 3, 6, and 9 days, respectively. 1×10⁵ cells/60 mm dish were seeded, and 24 hours later (Day 0), the medium was removed and fresh medium and additives were added then and every 48 hours thereafter. The arrow shows removal of additives. The triplicate cell count for each experimental point never varied by more than 10%.

Figure 4:
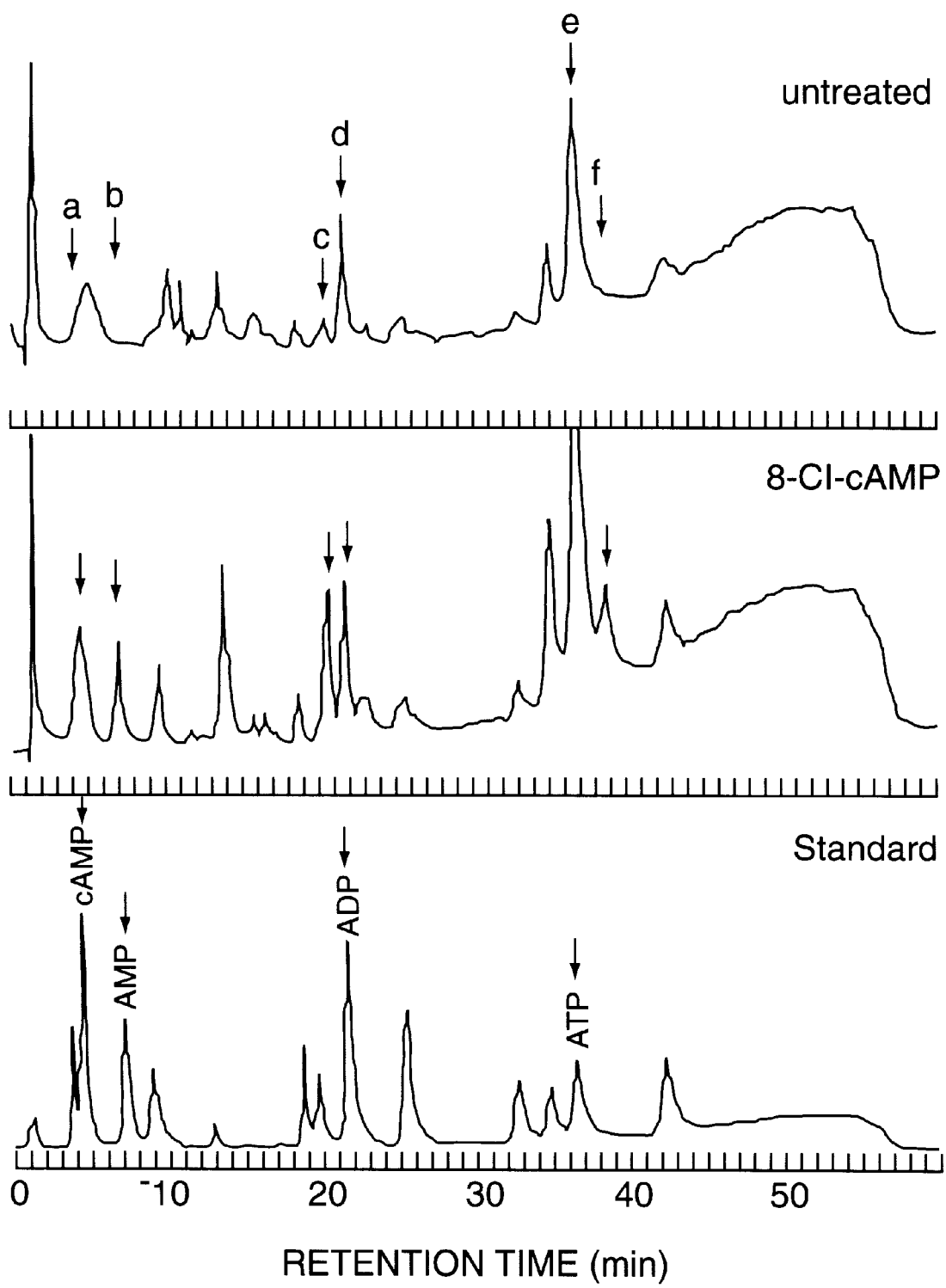

FIG. 4 shows the HPLC analysis of cell extracts after treatment of HT-29 colon cancer cells with 8-Cl-cAMP. HPLC analysis of nucleotides was performed on the cell extracts from cells treated for 72 hours with 8-Cl-cAMP (50 microM) and untreated control cells as described below.

FIG. 5 shows DEAE-Cellulose chromatography of the cytosols from cAMP analogue-treated and untreated LS-174 cells. Cytosols of untreated (A) and treated (for three days with 0.5 microM $N^6$-benzyl-cAMP+1 microM 8-Cl-cAMP) (B) cells were prepared, and the chromatography was performed as below. Δ, NaCl concentration. Protein kinase activity in the absence (●) and presence (○) of 5 microM cAMP and cAMP binding activity (▲) using 100 microL aliquots of each fraction measured as described below. A unit of enzyme activity of protein kinase was defined as that amount of enzyme that transferred 1 pmol of $^{32}P$ from [$^{32}P$]ATP to recovered protein in seven minutes at 30° C. in the standard assay. The cAMP binding was expressed as the specific binding calculated by the subtraction of a blank value (the amount of [3H]cAMP bound in the presence of excess nonradioactive cAMP) from the value obtained with radioactive nucleotide alone. The column profile represents one of several similar experiments.

Figure 6:
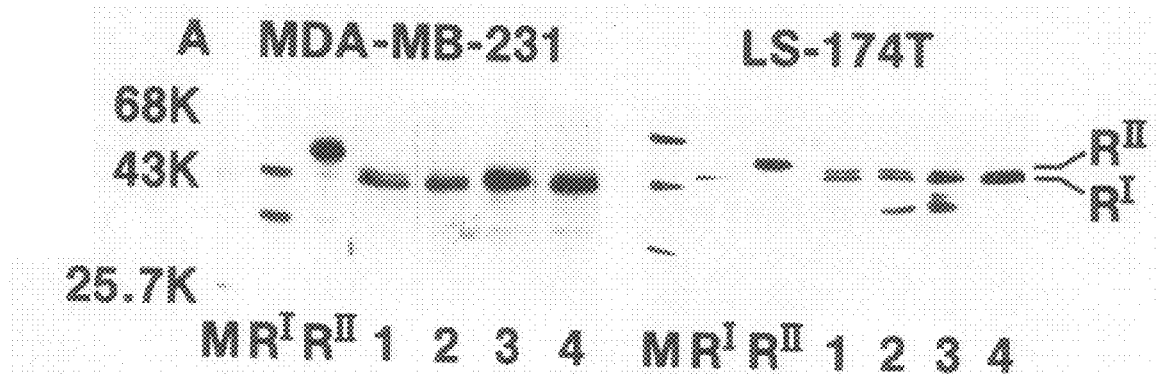

FIG. 6 shows the effects of cAMP analogue treatment on the $R^I$ $R^{II}$ receptor levels in breast (MDA-MB-231) and colon (LS-174T) cancer lines. Photoactivated incorporation of 8-$N_3$[$^{32}P$]cAMP was performed as described below. $R^I$, the 48,000 molecular weight $R^I$ cAMP receptor protein; $R^{II}$, the 56,000 molecular weight $R^{II}$ cAMP receptor protein.

In lanes 1, 2, and 3, cells were each treated for 3 days with 8-Cl-cAMP (10 microM), $N^6$-benzyl-cAMP (10 microM), and $N^6,O^{2'}$-dibutyryl-cAMP (1 mM), respectively; lane 4, untreated control cells. M is marker proteins of known molecular weight.

Each lane contained 50 micrograms protein for SDS-PAGE.

Figure 7:
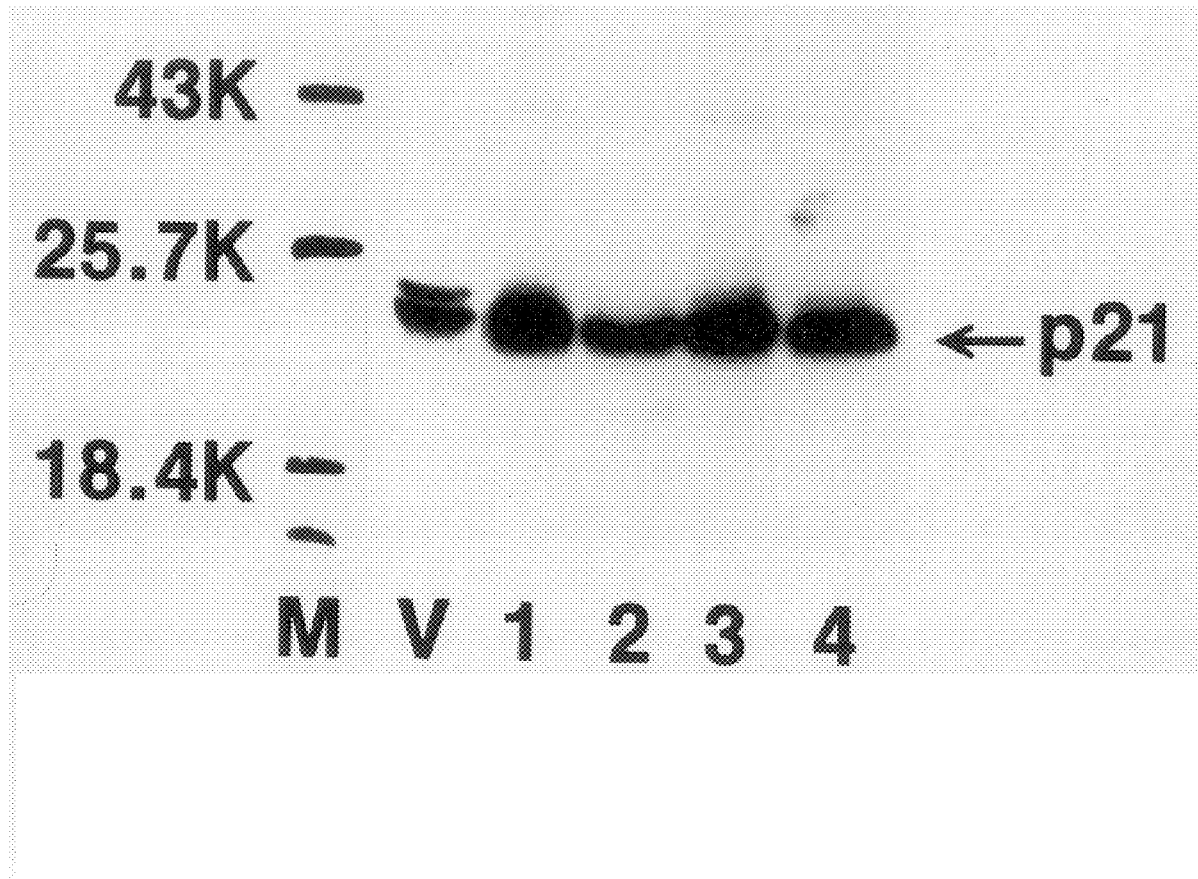

FIG. 7 shows the Western blotting of p21 ras protein in MCF-7 cells before and after cAMP analogue treatment. Western blotting of p21 protein was performed as described below. Lane 1 is the control; lanes 2, 3, and 4, cells treated for three days with 8-Cl-cAMP (10 microM), 8-Cl-adenosine (5 microM), and DBcAMP(500 microM), respectively. V is cell lysate from Ha-MuSV-transformed NIH3T3 clone 13-3B-4. M, marker proteins of known molecular weight.

Each lane contained 100 micrograms of protein for SDS-PAGE.

Figure 8A:
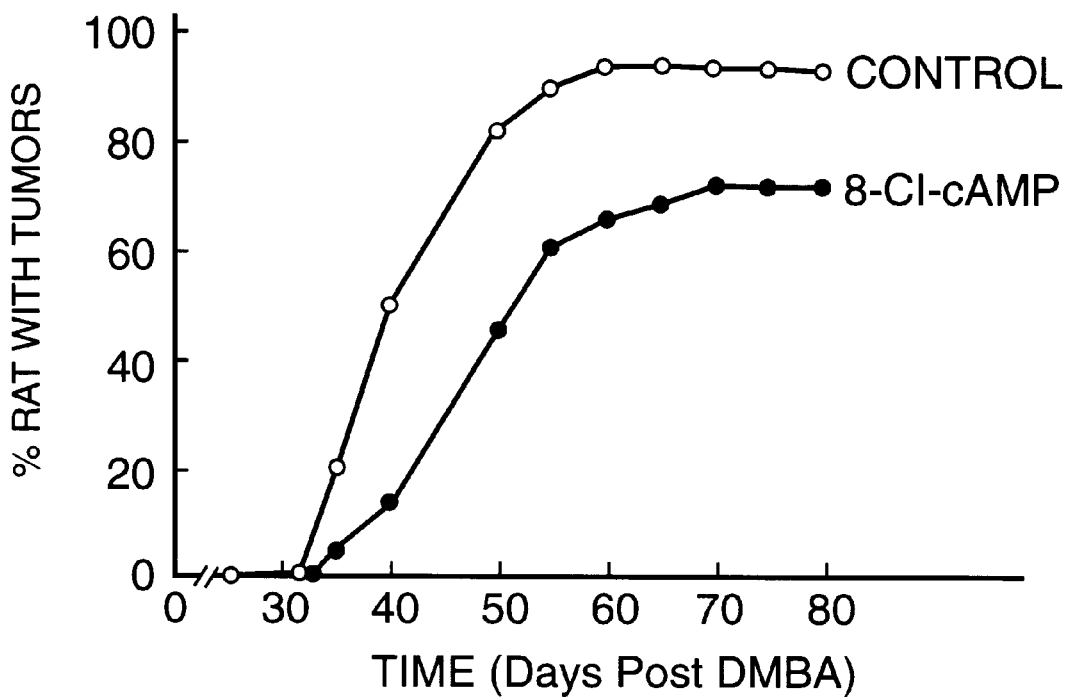
Figure 8B:
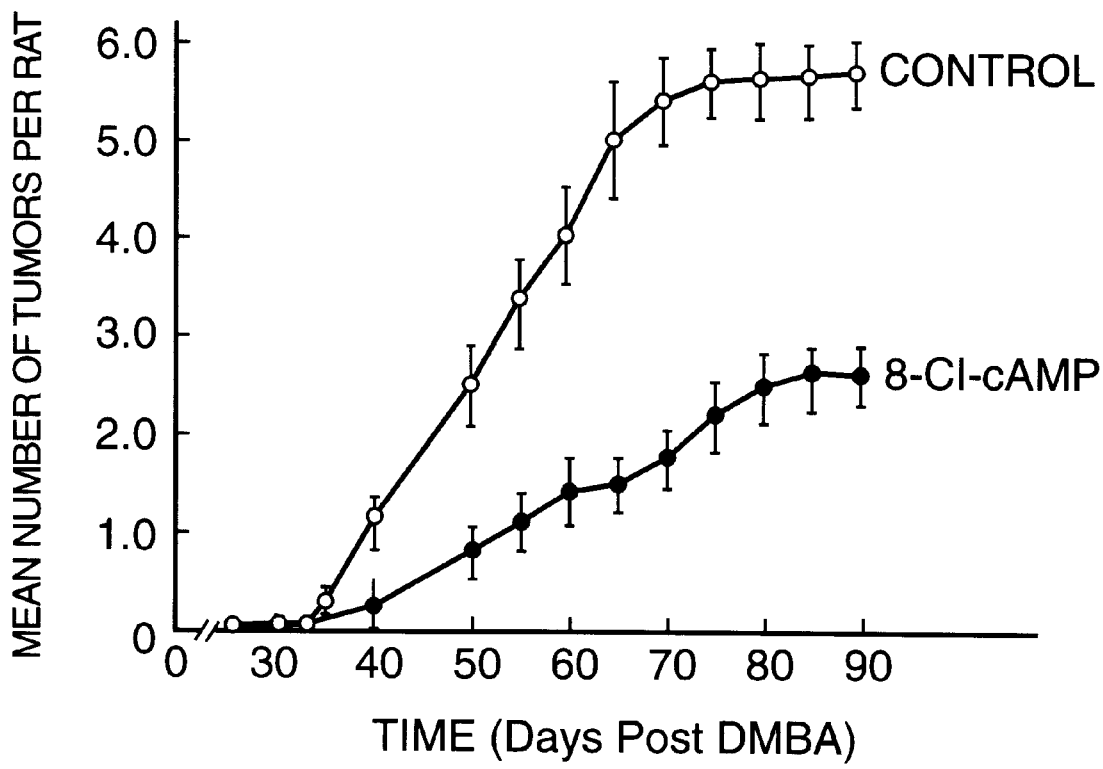

FIG. 8 shows the effect of 8-Cl-AMP pellet on the rate (A) and number (B) of mammary tumor inductions by DMBA.

FIG. 9 shows the effect of site-selective cAMP analogue treatment on the levels of cAMP receptor protein and c-myc protein.

DETAILED DESCRIPTION OF THE INVENTION

The compounds of the present invention have been found to be active against a variety of cancer cells, both in vitro and in vivo. The growth-regulating activity of the compounds and compositions of the present invention were studied using the cyclic nucleotide effector mechanisms involved in cAMP-mediated processes in vivo using a test to establish whether or not the cAMP receptor protein is the mediator of the response, and the compounds' binding to sites 1 and 2 is cooperative so that the compounds' sensitivity toward synergism for the binding to the cAMP receptor protein in intact cells can be measured.

If the compounds administered together demonstrate synergistic activity in inhibiting the growth of cancer cells, lower total concentrations of both compounds can be used to achieve the same cellular response obtained by otherwise using a single compound.

Cell Culture

All breast cancer cell lines were grown in IMEM supplemented with 10% fetal bovine serum, 20 mM HEPES, penicillin-streptomycin, and extra glutamine. Colon carcinoma cell lines were grown in EMEM supplemented with 10% FBS, EMEM, NEAA, HEPES 20 mM, extra glutamine, and penicillin-streptomycin. The cells were grown at 37° C. in humidified incubators in an atmosphere of 5% $CO_2$.

For cell growth experiments, 2–3×10⁵ cells/60 mm dish were seeded, and 24 hours later (Day 0), the medium was removed, and fresh medium and the additives were added then and every 48 hours thereafter The compounds of the present invention were added using 100× concentrated stock solutions. At desired times, cell counts in duplicate were performed on a Coulter counter after harvesting the cells with gentle trypsinization.

Preparation of Cell Extracts

All procedures were performed at 0–4° C. The cell pellets, consisting of $2\times10^7$ cells, after two washes with phosphate-buffered saline (PBS), were suspended in 0.5 ml buffer 10 (0.1 M NaCl, 5 mM MgCl2, 1% Nonidet P-40, 0.5% Na-deoxycholate, 2 KIU/ml bovine aprotinin, and 20 mM Tris-HCl, pH 7.4) and homogenized with a Dounce homogenizer for 100 strokes. The homogenates were centrifuged at 700×g for 20 minutes. The supernatants were used as cell extracts.

DEAE-Cellulose Chromatography of Protein Kinase

The cAMP-dependent protein kinase holoenzymes and the regulatory subunits were separated using DEAE-cellulose according to the method of Robinson-Steiner and Corbin (*J. Biol. Chem.* 258: 1032–1040, 1983). The cell pellets, of $2-4\times10^7$ cells, after two washes with PBS, were hand-homogenized in 3 ml of buffer B (10 mM potassium phosphate containing 1 mM EDTA at pH 6.8) with a Dounce homogenizer, 60 strokes. The homogenates were centrifuged for 20 minutes at 10,000×g. The resulting supernatants (2–2.5 ml) were loaded on a 0.9×5.0 cm column preequilibrated with buffer B. After washing, the column was eluted using 60 ml total volume gradient from 0 to 0.4 M NaCl in buffer B with 1.0–1.2 ml fraction volume.

Photoaffinity Labelling of cAMP Receptor Proteins

The photoactivated incorporation of 8-$N_3[^{32}P]$cAMP was performed as described by Pomerantz et al. (*Biochemistry* 14: 3858–3862, 1975) with a minor modification. The reaction mixtures, final volume of 50 microliters, contained $10^{-6}$ M 8-$N_3[^{32}P]\pm1000$-fold excess unlabelled cAMP and samples of 100–150 micrograms protein in buffer 10. The incubations were carried out at 23° C. for 60 minutes in 96-well immunoplates. The reaction mixtures were then irradiated for 30 seconds at 254 nm, placing a Mineralite UVS-11 hand lamp directly onto the plate. The samples were mixed with 25 microliters of 3× sample buffer (3% SDS, 15% beta-mercaptoethanol, 30 mM Tris, 30% glycerol, 1% bromophenol blue saturated solution), boiled for 3 minutes, and centrifuged at 700×g for five minutes. The samples containing 50–100 micrograms of protein were subjected to 0.05% SDS-12% PAGE. The gels were fixed, dried, and exposed to X-ray films overnight. The protein concentrations were determined by the method of Lowry et al., (*J. Biol. Chem.* 193: 265–275, 1951) with bovine serum albumin as standard.

Western Blotting of p21 Protein

Cellular proteins present in cell extracts were separated by 12% SDS-PAGE and transferred to nitrocellulose sheets in transfer buffer (25 mM Tris, 192 mM glycine, 20% methanol, pH 7.4). Nitrocellulose sheets were washed and first incubated with 3% bovine serum albumin in NTE-NP40 (50 mM Tris-HCl, pH 7.5, 150 mM NaCl, 2 mM EDTA, 0.1% Nonidet P-40) for three hours at 37° C. and then sequentially incubated with medium containing p21 monoclonal antiserum Y13-259 directed against the Ha-MuSV-encoded p21 for sixteen hours at 4° C., rabbit anti-rat IgG for 2.5 hours in an ice-water bath, and $5\times10^5$ cpm/ml $^{125}$I-protein A for one hour in an ice-water bath. The nitrocellulose sheets were air-dried and exposed to Kodak XAR film for 12–36 hours at −20° C. Comparison of the resulting autoradiograms with others in which normal rat serum was substituted for p21 monoclonal antibody permitted identification of p21. To provide a reference p21, cell lysates were prepared from NIH 3T3 clone 13-3B-4 that had been transfected with Ha-MuSV DNA.

High-Performance Liquid Chromatography

The cells were washed twice with PBS (centrifuged each time at 700×g for five minutes), and the pellets were suspended in 0.4 N perchloric acid ($2\times10^7$ cells/ml), vortexed, and centrifuged as above. The supernatant was neutralized with 3.5 M potassium bicarbonate (57 microliters/ml perchloric acid), vortexed, and centrifuged as above. The supernatants were used in HPLC (100 microliter injections) after filtering through HPLC nylon filters (3 mm/0.45 micrometer pore size).

HPLC was performed using a Varian 5500 chromatograph equipped with a Rheodyne model 7125 sample injector, a strong anion exchanger column 12.5 cm, and an LKB 2140 rapid spectral diode array. The nucleotides were eluted with a linear gradient from 0.01 M $KH_2PO_4$ (pH 3.83) to 0.8 M $KH_2PO_4$ (pH 3.5). The solvent flow rate was 1.0 ml/min. The column effluent was monitored by the spectra detector between 190 and 370 nm (with 1 nm and 1-s intervals) for 60 minutes. Retention times, peak areas, and absorption spectra were determined by a laboratory computer using LKB 2140-260 COMPARE software.

Cell Cycle Analysis

DNA histograms were generated on FACS II by using the DNA intercalating dye propidium iodide as described by Braylan et al. (*Cytometry* 2: 337–343, 1982). The percentage of cells in each cycle phase was calculated by using a PDP-11/34 computer and software as described by Neckers et al. (*Mol. Cell. Biol.* 6: 4244–4250, 1986).

Effect of Site-Selective cAMP Analogues on Growth Inhibition

A variety of cAMP analogues, modified at either the C-6 or C-8 position or both the C-6 and C-8 positions of the adenine moiety, were tested for their growth inhibitory effect on cancer cell lines. The studies reported in Table I were carried out by measuring cell growth by counting the cell number at Day 3 and Day 4 after treatment of the cells with each individual compound at several concentrations on Day 0 and Day 2. Cell counts were performed on each of three or more separate experiments, and the average values are expressed as percent growth inhibition as compared with untreated control cells.

TABLE 1

Effect of site-selective cAMP analogues on the growth of breast (MCF-7) and (LS-174T) colon cancer cell lines
cAMP Analogues are listed in order from the most to the least potent for a given modification on the adenine ring

| | | % Growth Inhibition[a] | |
|---|---|---|---|
| Cyclic nucleotide analogue added (50 μM) | | Day 3 | Day 4 |
| C-8 | 8-Chloro | 67(62–75) | 75(68–81) |
| | 8-Methylthio | 46(42–52) | 42(38–50) |
| | 8-Bromo | 41(37–44) | 40(35–45) |
| | 8-Iodo | 26(20–31) | 25(23–27) |
| | 8-p-chlorophenylthio | 23(19–27) | 24(20–26) |
| | 8-βhydroxyethylamino | 15(12–17) | 20(15–23) |
| | 8-Methylamino | 14(10–16) | 15(12–18) |
| | 8-N,N-Dimethylamino | 0(0) | 0(0) |

TABLE 1-continued

Effect of site-selective cAMP analogues on the growth of breast
(MCF-7) and (LS-174T) colon cancer cell lines
cAMP Analogues are listed in order from the most to the least
potent for a given modification on the adenine ring

| Cyclic nucleotide analogue added (50 μM) | % Growth Inhibition[a] Day 3 | Day 4 |
|---|---|---|
| C-6 N$^6$-Benzyl | 56(49–60) | 70(65–74) |
| N$^6$-Ethoxycarbonyl | 32(27–40) | 40(36–43) |
| N$^6$-Benzoyl | 30(26–38) | 28(25–32) |
| N$^6$-Phenylcarbamoyl | 10(8–12) | 10(5–12) |
| N$^6$-Butyryl | 0(0) | 0(0) |
| N$^6$,O$^{2'}$-Dibutyryl | 0(0) | 0(0) |
| C-6,-8 N$^6$-Phenyl-8-p-chlorophenylthio | 60(56–63) | 47(44–55) |
| N$^6$,N$^6$-Diethyl-8-p-chlorophenylthio | 43(40–50) | 45(40–49) |
| 6-Piperidino-8-p-chlorophenylthio | 33(30–37) | 25(21–30) |
| N$^6$-Benzyl-8-benzylthio | 25(20–30) | 23(20–25) |
| N$^6$-n-Butyl-8-p-chlorophenylthio | 15(12–17) | 22(20–24) |

[a]The values of percentage growth inhibition were determined from the dose-response curve experiments. Each value represents an average value and range (in parentheses) obtained from three or more separate experiments. The cell counts in duplicate were performed at day 3 and day 4 after two treatments (day 0 and day 2) with analogs (seeding on day −1).

Table 1 above shows the growth inhibitory effect of 19 site-selective compounds on the breast (MCF-7) and colon (LS-174T) cancer cell lines. The compounds are listed in order from the most to the least potent for growth inhibition for a given modification on the adenine ring. As shown in Table I, analogues modified with a halogen or thio moiety at the C-8 position were more potent than those modified with an amino moiety at the C-8 position. Thus, at 50 micromolar concentration, 8-Cl-, 8-methylthio-, and 8-bromo-cAMP exhibited 40–75% growth inhibition, while 8-beta-hydroxylamino-, 8-methylamino-, and 8-N,N-dimethylamino-cAMP exhibited growth inhibition of only ≦20%. C-6 analogues were generally less potent in growth inhibition than the C-8 analogues and C-6, C-8 analogues were even less potent. At 50 micromolar concentration, N$^6$-benzyl-, and N$^6$-ethoxycarbonyl-cAMP demonstrated 30–70% growth inhibition. Dibutyryl cAMP, an earlier known analogue, at 50 micromolar concentration, exhibited no growth inhibition. The C-6,-8-analogue, N$^6$-phenyl-8-p-chlorophenylthio-cAMP, which is structurally similar to both N$^6$-benzyl- and 8-Cl-cAMP, exhibited the most potent growth inhibition among the C-6,-8 disubstituted analogues.

Figure 1:
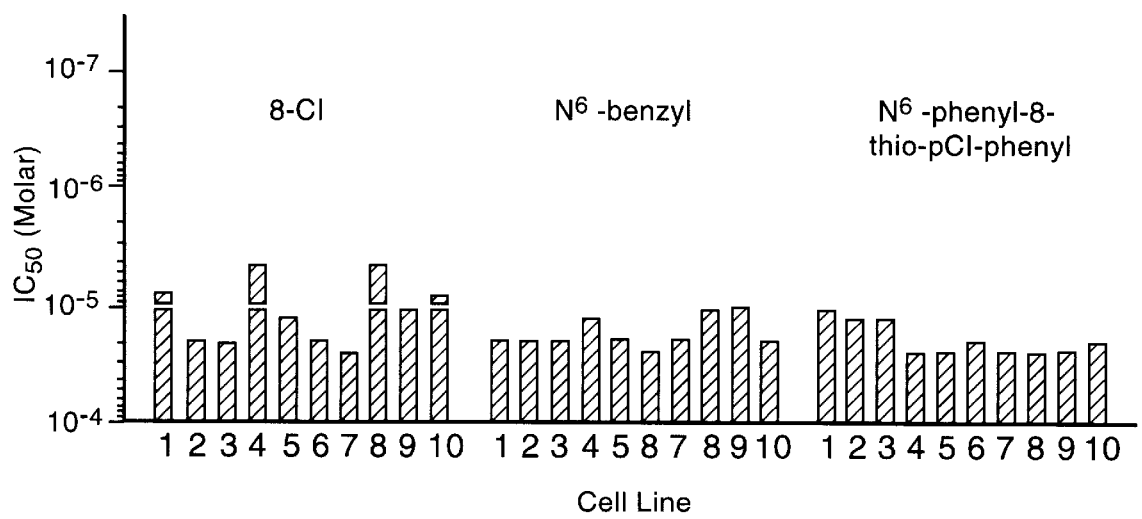
FIG. 1 shows the growth inhibition of breast and colon cancer lines by site-selective cAMP analogues.
Figure 2A:
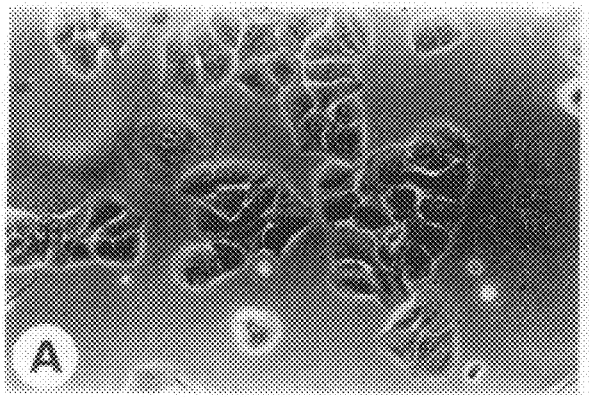
Figure 2B:
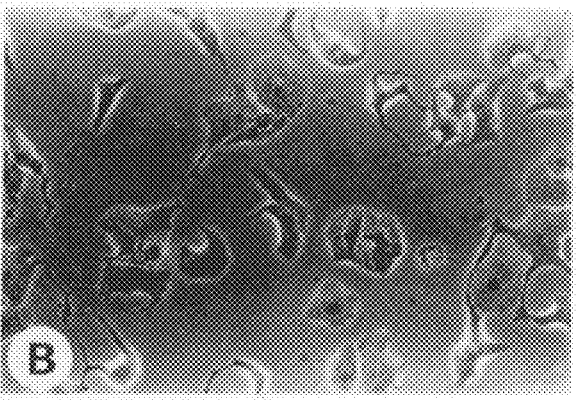
Figure 2C:
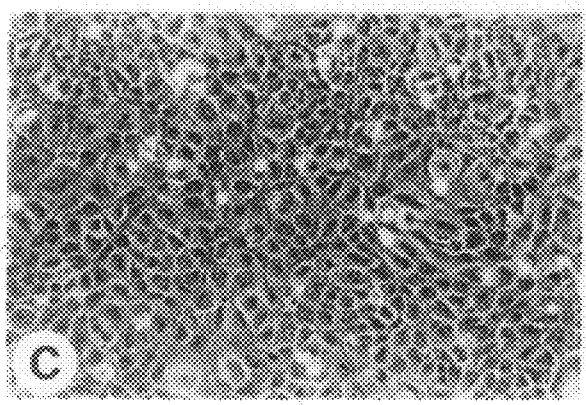
Figure 2D:
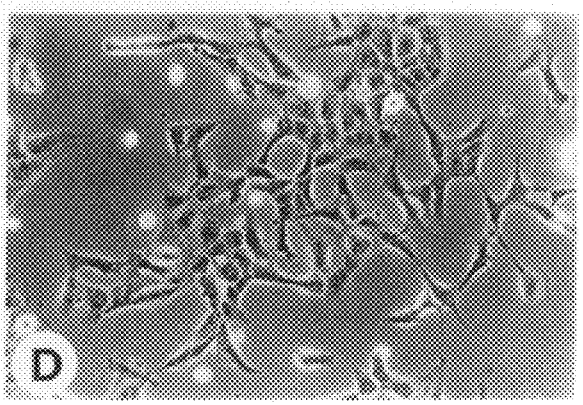

FIG. 1 shows the growth inhibitory effect of the three most potent compounds, 8-Cl, N$^6$-benzyl-, and N$^6$-phenyl-8-p-chlorophenylthio-cAMP, on the breast and colon cancer lines. These analogues demonstrated 50% growth inhibition at 5–25×10$^{31\ 6}$ to 2.5×10$^{-5}$ M concentrations (IC$_{50}$) in all ten cancer lines tested. Thus, the site-selective compounds exhibited potent growth inhibition in the hormone-dependent (MCF-7, T-47D, ZR-75-1) and hormone-independent (MDA-MB-231, MCF-7ras, BT-20) breast cancer lines as well as colon cancer lines at micromolar concentrations. As previously reported by (Cho-Chung, Cell. Mol. Biol. 26:395–403, 1980, Cho-Chung et al., Science 214:77–79, 1981; and Fentiman et al., Mol. Biol. Med. 2:81–88, 1984); dibutyryl cAMP or N$^6$-butyryl cAMP at millimolar concentrations showed growth inhibition only in the hormone-dependent breast cancer lines but not in the hormone-independent breast and colon cancer cell lines. Phosphodiesterase inhibitors, such as theophylline (0.1 mM) or 1-methyl-3-isobutylxanthine (0.5. mM), alone each had little or no growth inhibitory effect, particularly on the hormone-independent breast and colon cancer lines, and these inhibitors could not enhance the effect of the site-selective compounds even when added in combination with the site-selective compounds. The effect of the site-selective cAMP analogues on growth inhibition appears to be more selective toward transformed cancer cells than nontransformed cells, since the site-selective compounds were 50–70% less potent for nontransformed NIH/3T3 cells compared with the Ha-MuSV-transformed NIH/3T3 clone 13-3B-4 cells.

Effect of Combinations of Compounds on Growth Inhibition

Previous in vitro studies have demonstrated that binding of a cAMP analogue selective for either intrachain site on the regulatory subunit of protein kinase stimulates binding of a cAMP analogue selective for the other site (Rannels et al., J. Biol. Chem. 256:7871–7876, 1981; and Corbin et al., Eur. J. Biochem. 125:259–266, 1982), and two such site-selective compounds in combination demonstrate synergism on protein kinase activation (Robinson-Steiner et al., J. Biol. Chem. 258:1032–1040, 1983; and Ogreid et al., Eur. J. Biochem. 150:219–227, 1985). Synergism of two classes of site-selective cAMP analogues has been demonstrated in lipolysis in isolated adipocytes by Beebe et al. (J. Biol. Chem. 259:3539–3547, 1984) and in growth inhibition of HaMuSV-transformed NIH 3T3 cells (Tagliaferri et al., Biochem. Biophys. Res. Commun. 130:1193–1200, 1985).

To test the effect of cAMP analogue combinations, C-8 analogues, which are site 1-selective, and C-6 analogues, which are site 2-selective, were combined such that alone their exhibit growth inhibition of 10–20% each, and the effects were quantified by synergism quotient. Synergism quotient was defined as the net growth inhibitory effect of the analogue combination divided by the sum of the net analogue effects on growth inhibition A quotient of >1 indicates a synergistic effect, while a quotient of <1 indicates an antagonistic effect. Considering especially that the C-6, C-8 compounds are less potent than either the C-6 or C-8 compounds, it is most surprising that co-use of C-6 and C-8 compounds is even better than the use of either C-6 or C-8 compounds alone.

Table 2 shows representative examples of synergism between C-6 and C-8 analogues in growth inhibition of the MCF-7 ras cell line. 8-Cl-cAMP (1 microM), in combination with either N$^6$-benzyl- or N$^6$-benzoyl-cAMP, produced the greatest degree of growth inhibition compared with that expected from the sum of the individual analogues alone, having a synergism quotient of 1.71 to 1.83. 8-Cl-cAMP, in combination with either N$^6$-benzyl- or N$^6$-benzoyl-cAMP (0.5 microM), therefore, produced the growth inhibitory effect that is almost equivalent to that shown by 20–20 microM concentrations of either 8-Cl-cAMP or the N$^6$-analogues alone. The N$^6$-analogues also demonstrated synergism of growth inhibition with other c-8 analogues, such as 8-methylthio-cAMP (synergism quotient 1.50–1.84) and 8-bromo-cAMP (synergism quotient 1.5). Only a limited degree of synergism was noted, however, when the N$^6$-analogues were combined with 8-amino derivatives (synergism quotient 1.12–1.25). Thus, the N$^6$-analogues acted far more synergistically when in combination with 8-thio or 8-halogen derivatives than with 8-amino derivatives. Similar synergism of growth inhibition by the C-6 and C-8 analogue combination was also demonstrated in other breast and colon cancer cell lines. Synergism of growth inhibition was only seen when a site 1-selective analogue was added with a site 2-selective analogue, but not when two site 1-selective or two site 2-selective analogues were combined. Two such examples are shown in Table 2.

TABLE 2

Synergistic growth inhibitory effect of C-6 and C-8
analogue combination in MCF-7 ras breast cancer cell line
Synergism of growth inhibition was determined by treatment of
cells with C-6 analogues and C-8 analogues alone and in combination at
Day 0 and Day 2 and counting the cell number at Day 4

| Analogue combination | $\mu$M | % Growth inhibition[a] | Synergism quotient[b] |
|---|---|---|---|
| 8-Chloro + | 1.0 | 60(57–62) | 1.71 |
| N[6]-Benzyl | 0.5 | | |
| 8-Chloro + | 1.0 | 55(47–57) | 1.83 |
| N[6]-Benzoyl | 0.5 | | |
| 8-Methylthio + | 1.0 | 45(40–52) | 1.50 |
| N[6]-Benzyl | 0.5 | | |
| 8-Methylthio + | 1.0 | 46(40–55) | 1.84 |
| N[6]-Benzoyl | 0.5 | | |
| 8-Methylamino + | 1.0 | 28(20–30) | 1.12 |
| N[6]-Benzyl | 0.5 | | |
| 8-Methylamino + | 1.0 | 25(20–27) | 1.25 |
| N[6]-Benzoyl | 0.5 | | |
| 8-Chloro + | 1.0 | 30(22–32) | 0.86 |
| 8-Methylthio | 1.0 | | |
| N[6]-Benzyl + | 0.5 | 20(18–25) | 0.80 |
| N[6]-Benzoyl | 0.5 | | |

[a]Data are expressed as percentage growth inhibition in reference to the growth of untreated control cells and represent average values and ranges (in parentheses) of duplicate cell counts on three or more separate experiments. The values for percentage growth inhibition of each analogue, when added alone, were 20% (8-Cl-cAMP), 15% (methylthio-cAMP), 10% (8-methylamino-cAMP), 15% (N[6]-benzyl-cAMP), and 10% (N[6]-benzoyl-cAMP).
[b]The synergism quotient was defined as previously described.

Effect of cAMP Analogues on Cell Morphology

The growth inhibitory effect of the site-selective cAMP analogue correlated with a change in the cell morphology. As shown in FIG. 2, both hormone-dependent (A) and -independent breast (C, E, and G) cancer cells demonstrated a characteristic morphological change after treatment with 50 microM 8-Cl-cAMP for four to five days. The cells exhibited an enlargement of cytoplasm with stretched fibroblast-like appearance (B, D, F and H) Treatment of breast and colon cancer cells with N[6]-benzyl-cAMP (50 microM), and 8-methylthio-cAMP (100 microM) for three to four days all induced the morphological change. Furthermore, the synergistic growth inhibitory effect of C-6 and C-8 analogue combinations was also reflected in the change in the cell morphology. Thus, treatment of cells with either 1 microM 8-Cl-cAMP or 0.5 microM N[6]-benzyl-cAMP for four days did not induce a change in the cell morphology, whereas when the cells were treated in combination with 8-Cl-cAMP (1 microM) and N[6]-benzyl-cAMP (0.5 microM), the cells exhibited the morphological change. The same synergism was demonstrated between the other N[6]-analogues and C-8 analogues that demonstrated the synergism of growth inhibition.

Effect of 8-Cl-cAMP and 8-Cl-Adenosine on Growth and Cell Cycle Progression

The growth inhibitory effect of the site-selective cAMP analogues was examined to determine if there was also a cytotoxic effect due to an adenosine metabolite. FIG. 3 shows time courses of 8-Cl-cAMP and 8-Cl-adenosine in their growth inhibition and release from the inhibition in the LS-174T colon cancer line, While the untreated control cells showed a logarithmic increase in cell number, cells treated with either 8-Cl-cAMP or 8-Cl-adenosine exhibited a marked reduction in cell growth and eventually stopped replicating within three to four days. Upon cessation of treatment, the cells treated with either 8-Cl-cAMP for up to nine days resumed growth almost immediately, and the rate of cell growth became similar to that of untreated control cells within a few days, whereas the 8-Cl-adenosine-treated cells remained growth-inhibited and did not resume their growth up to two weeks after the release from the treatment. Thus, the growth inhibition produced by 8-Cl-cAMP and 8-Cl-adenosine was mediated through two different mechanisms; the former by a decrease in the rate of replication without affecting cell viability, and the latter by cell killing.

A determination was made whether the reduced cell proliferation observed in the cancer cell lines after treatment with the compounds of the present invention is due to a specific block in one phase of the cell cycle. As shown in Table 3, the fractions of cells in G1, S, and G2/M phases were not appreciably different between the control cells (untreated) and the cells treated with either 8-Cl-cAMP or N[6]-benzyl-cAMP. Thus, the inhibition of cell growth induced by the cAMP analogues was not associated with a specific block in one phase of the cell cycle. However, 8-Cl-adenosine treatment induced an appreciable increase of the cell population in G1 phase with a marked reduction in S-phase.

TABLE 3

Effect of site-selective cAMP analogues and
8-Cl-adenosine on cell cycle progression of breast
and colon cancer cell lines
Breast (MCF-7, MDA-MB-231) and colon (LS-174T) cancer cells in
log phase (untreated control) and 3 days after treatment with
8-Cl-cAMP (10 $\mu$M) N[6]-benzyl-cAMP (35 $\mu$M) and 8-Cl-adenosine
(5 $\mu$M) were analyzed for DNA content by flow cytometric analysis
as described below
Similar results were obtained with other
breast and colon cancer cell lines

| | | % Cell population in: | | | % |
|---|---|---|---|---|---|
| Cell line | Treatment | $G_1$ | S | $G_2$M | Growth |
| MCF-7 | Control | 52 | 23 | 25 | 100 |
| | 8-Cl (10 $\mu$M) | 53 | 22 | 25 | 40 |
| MDA-MB-231 | Control | 57 | 25 | 18 | 100 |
| | N[6]-benzyl (35 $\mu$M) | 60 | 25 | 15 | 45 |
| LS-174T | Control | 60,52[a] | 17,23 | 23,25 | 100,100 |
| | 8-Cl (10 $\mu$M) | 63,53 | 15,22 | 22,25 | 30,32 |
| | 8-Cl-adenosine (5 $\mu$M) | 72,68 | 8,14 | 20,18 | 30,30 |

[a]The paired numbers were derived from two separate experiments.

HPLC Analysis of Cell Extracts After Treatment of Cancer Cells with cAMP Analogues As shown in FIG. 4, the cell extracts from the HT-29 colon cancer cell line treated for 72 hours with 50 microM 8-Cl-cAMP demonstrated several distinct peaks that are not present in the untreated control cell extracts. In reference to the elution profiles of the standard nucleotides, these peaks were identified to be 8-Cl-cAMP (peak a), 8-Cl-AMP (peak b), 8-Cl-ADP (peak c), and 8-Cl-ATP (peak f). The peak at approximately 1.5 minutes retention time was identical in both treated and untreated cell extracts. This peak would contain adenosine and 8-Cl-adenosine if they were present in the sample. In fact, no 8-Cl-adenosine was present in this peak as verified by absorption spectra. In the medium from the cells treated for 49 hours with 8-Cl-cAMP (50 microM), a single large peak of 8-Cl-cAMP was detected, but no 8-Cl-adenosine was present. These data showed that the intact 8-Cl-cAMP, without being metabolized by the membrane-bound phosphodiesterase, penetrated the cell, and a portion of 8-Cl-cAMP was converted to 8-Cl-AMP, 8-Cl-ADP and 8-Cl-ATP. Treatment of cells with 8-Cl-AMP at concentrations as high as 100 microM, however, produced no appreciable growth inhibition.

Figure 5A:
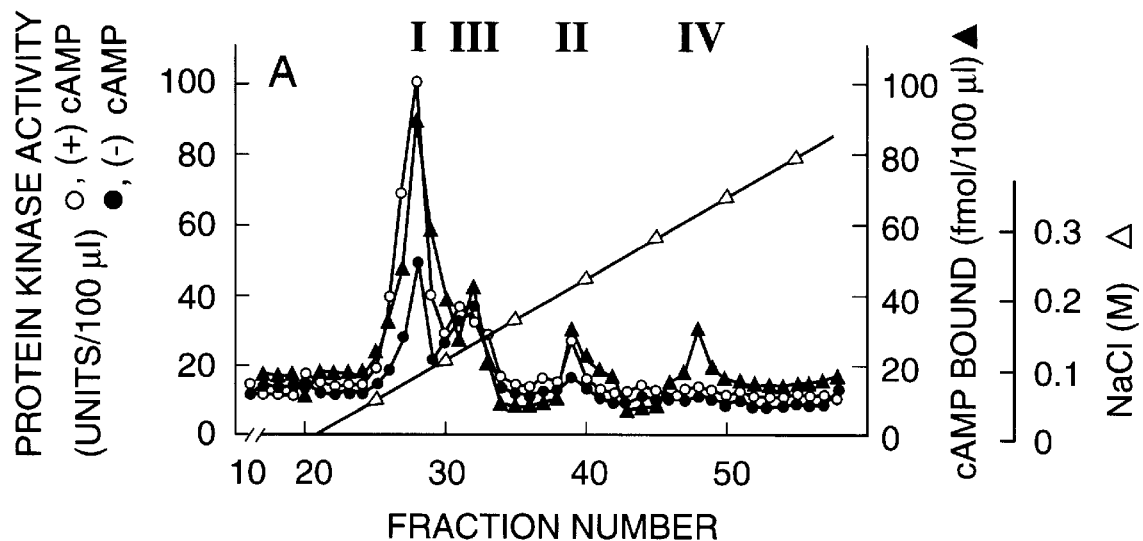

The Effect of cAMP Analogues on the Levels of $R^I$ and $R^{II}$ cAMP Receptor Proteins The synergistic effect demonstrated on the growth inhibition of the cancer cells by the C-6 and C-8 thio or C-8 halogen derivatives of cAMP analogues in combination indicated a response of type II protein kinase, rather than type I kinase, in the analogue effect. The relative proportions of free $R^I$ and $R^{II}$ and holoprotein kinases, type I and type II, were determined using DEAE-cellulose chromatography. Chromatography of the cytosols from treated and untreated LS-174T cells is shown in FIG. 5. The catalytic subunit was eluted before the start of the NaCl gradient. The untreated cells, FIG. 5A, showed two major peaks, peaks 1 and 2, of cAMP-dependent protein kinase activity that were coincident with peaks of cAMP binding activity. Peak 1 eluted at 0.07 M NaCl, and peak 2 eluted at 0.22 M NaCl, and the kinase and binding activities of peak 1 were approximately three-fold that of peak 2. In addition, two minor cAMP binding peaks, peaks 3 and 4, with no cAMP-dependent protein kinase activity eluted at 0.13 M NaCl and 0.30 M NaCl, respectively. Radioautography after photoaffinity labelling of the fractions of the eluents with 8-azido-[$^{32}$P] cAMP and performing SDS-PAGE showed that peaks 1 and 3 contained the 48,000 MrR$^I$, whereas peaks 2 and 4 contained the 52,000 MrR$^{II}$. These results suggest that peaks 1 and 2 are similar to types I and II holoprotein kinases, and peaks 3 and 4 are similar to free $R^I$ and $R^{II}$ subunits found in mammalian tissue cytosols.

Figure 5B:
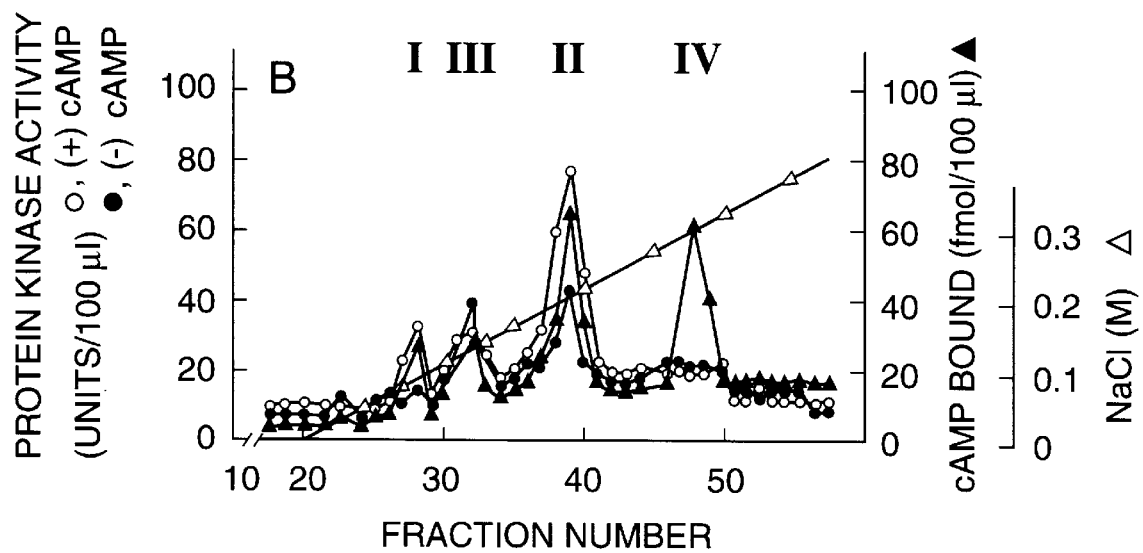

When the cells were treated for three days with $N^6$-benzyl-cAMP (0.5 microM) plus 1 microM of 8-Cl-cAMP, the chromatographic pattern was considerably altered, as shown in FIG. 5B. Both cAMP-dependent protein kinase activity and cAMP binding activity of peak 1 decreased to 30% of those in the untreated cells, while the cAMP-stimulated kinase and cAMP binding activities of peak 2 increased three-fold and two-fold, respectively. In addition, peak 4 cAMP binding activity increased two-fold over that of untreated control cells, while peak 3 remained without appreciable change. Thus, decrease of type I holoenzyme, peak 1, was accompanied by an increase of both type II holoenzyme, peak 2, and $R^{II}$ subunit, peak 4. A similar change in the elution profile was observed when the cells were treated with other combinations of C-6 and C-8 analogues that showed synergism in growth inhibition, whereas each of these compounds alone, at 1 microM concentration, exhibiting little or no growth inhibition, caused no apparent change in the elution profile. Thus, the same synergism of C-6 and C-8 analogue combinations was observed in protein kinase change as that observed for growth inhibition. When intact untreated cells were washed just before collection with the analogue combination-containing medium, the elution profile was the same as that of cytosol from untreated cells. Thus, the change in peaks 1, 2, and 4 observed in the analogue-treated cells was not a consequence of residual analogue from the medium interacting with the cytosol during cell homogenization.

The increase in peaks 2 and 4 observed after the analogue treatment suggests that the analogue caused both dissociation and increase of type II protein kinase. Furthermore, the presence in the treated cells of a considerable amount of type II holoenzyme, peak 2, suggests that peak 2, at least in part, may contain a partially dissociated form of holoenzyme, such as $R_2C$, which may not be resolved from $R_2C_2$ by DEAE-cellulose chromatography.

Since the type I and type II protein kinases differ only in their regulatory subunits, i.e., the cAMP binding receptor protein, while the catalytic subunits are identical, the receptor protein was measured during treatment of the cancer cells.

As shown in FIG. 6, the untreated breast (MDA-MB-231) and colon (LS-1741) cancer cells contained a major cAMP receptor protein with a Mr of 48,000, lane 4. This protein appears to be the $R^I$ cAMP receptor protein, i.e., the regulatory subunit of type I kinase, because it comigrated in SDS-PAGE with the purified preparation of the 48,000 MrR$^I$ (lane R$^I$) from rabbit skeletal muscle. When the cells were treated for three days with 8-Cl-cAMP, lane 1, or $N^6$-benzyl-cAMP (lane 2), the cAMP receptor protein with a molecular weight of 52,000 increased appreciably with concomitant decrease of the 48,000 $R^I$ receptor protein. The 52,000 Mr protein appears to be the $R^{II}$ cAMP receptor protein because the Mr 50,000–52,000 cAMP receptor proteins have been identified as the $R^{II}$ receptor protein in various tissues. When the cells were treated with DBcAMP, which did not inhibit cell growth, the $R^I$ and $R^{II}$ receptor levels remained unchanged, as can be seen by comparing lane 3 with lane 4.

Quantification by densitometric tracings of the autoradiograms showed that the cancer lines treated with 8-Cl-cAMP or $N^6$-benzyl-cAMP, exhibiting 45–70% growth inhibition, demonstrated a 70–80% decrease in the $R^I$ level and a two- to three-fold increase in the ratio of $R^{II}$ to $R^I$. DBcAMP in a concentration of 1 mM, a weak growth inhibitor (15%), did not appreciably affect the $R^I$ or $R^{II}$ receptor levels, as shown in Table 10.

Effect of cAMP Analogues on the p21 ras Protein Level

The site-selective cAMP analogues of the present invention have been found to bring about a reduction in the level of a cellular transforming gene product, p21 ras protein, in parallel to their growth inhibitory effect. As shown in FIG. 7, Western blotting analysis of p21 protein demonstrated that the MCF-7 cells treated with 10 microM 8-Cl-cAMP for three days, exhibiting 57% growth inhibition (cf. Table 11), contained a markedly decreased level of p21, as shown in FIG. 7, lane 2. A similar decrease in p21 protein was observed in the cells treated with $N^6$-benzyl-cAMP. A weaker growth inhibitor, DBcAMP (500 microM), which produced only 20% growth inhibition, as shown in Table 11, caused a slight reduction in p21 level, lane 4. 8-Cl-adenosine, 5 microM, though exhibiting strong growth inhibition, did not appreciably affect the p21 level, as shown in lane 3 of FIG. 7. Thus, 8-Cl-adenosine, producing growth inhibition through a different mechanism from that of 8-Cl-cAMP, failed to produce a biochemical change inducible with the cAMP analogues.

Effect of 8-Cl-cAMP on In Vivo Tumor Growth

The antitumor activity of 8-Cl-cAMP has been evaluated in a number of in vivo experimental tumor models. Initial data obtained with the intraperitoneally inoculated L1210 leukemia and intraperitoneal treatment suggested that a sustained presence of the cAMP derivative was required for antitumor activity. The maximum non-lethal dosage of the compound in non-tumored BDF$_1$ mice was 104 mg/kg. This dosage, when given as a bolus injection for seven consecutive days, was tolerated by L1210-bearing mice but demonstrated no antitumor effect. However, constant infusion of the cyclic nucleotide at a dosage of 104 mg/kg/day for five days caused a 37% increase in mean life span.

Based on the findings with the L1210 leukemia model, the efficacy of the 8-Cl-cAMP-Na+ infusions were evaluated in advanced-stage human tumor xenograft models. Tumor fragments of approximately 14 mg were implanted subcutaneously in athymic CD-1 female mice and seven day intraperitoneal infusions of the cyclic nucleotide were initiated three weeks later when mean tumor weights had reached 300–400 mg. Tumor measurements were recorded on the initial day of treatment (staging day) and one day after treatment was completed (staging day+7), and were used to calculate changes in tumor weights. The data obtained with two mammary, one lung, and one colon tumor (cf. Tables 8 and 9) indicated that infusions of 8-Cl-cAMP-Na$^+$ caused tumor stasis during treatment. In another study, a subcutaneous infusion of approximately 42 mg/kg/day (1 mg/mouse) for seven days appeared to be toxic to athymic NCR-NU mice bearing advance-stage human LoVo colon tumors of about 300 mg. An infusion of 0.67 mg/mouse/day caused only a minor tumor growth delay. In short-term assays (seven days) using the transplantable DMBA-1 and MNA-2 rat mammary carcinomas, it was found that pellets of 8-Cl-cAMP implanted at the time of tumor transplantation caused 40–50% inhibition of tumor growth.

As shown in Table 4, the 8-Cl-cAMP 10 mg pellet implanted twice every two weeks completely stopped tumor growth. Treated tumors regress almost 100% within 30 days. DBcAMP treatment only arrests this tumor growth without producing regression.

TABLE 4

Effect of 8-Cl-cAMP pellet on the in vivo growth of DMBA-induced mammary carcinomas in rats

| Treatment | Total tumor no. | Mean tumor measurement (cm) Day 0 | Mean tumor measurement (cm) Day 30 | Mean % of change in tumor volume |
|---|---|---|---|---|
| none | 20 | 1.2 × 1.5 | 2.2 × 3.2 | +760 + 150[a] |
| 8-Cl pellet[b] | 20 | 1.3 × 1.8 | 0.3 × 0.5 | −96 + 20 |

[a]Mean ± S.E.
[b]8-Cl-cAMP (20 mg. pellet per rat, consisting of 10 mg 8-Cl-cAMP and 10 mg. cholesterol), was implanted on day 0 and day 14.

As shown in Table 5, these tumors are completely resistant to DB-cAMP, whereas the 8-Cl-cAMP 10-mg pellet caused 40–50% growth inhibition within one week. A continuous supply of 8-Cl-cAMP with an osmotic pump may produce greater inhibitory effect. Alternatively, the compound may be administered in time-release form or in time-release liposomes.

As shown in FIG. 8, 8-Cl-cAMP (10 mg pellet) implantation one day before the carcinogen DMBA intubation resulted in 30 days of delay in the first tumor appearance and 70% reduction in the total number of tumors produced as compared with the effect of DMBA only. The results indicate the effect of 8-Cl-cAMP on blocking of the initiation stage of DMBA carcinogenesis.

The following data show the effect of 8-Cl-cAMP on the growth of malignant neoplasms in vivo:

TABLE 5

Effect of 8-Cl-cAMP pellet in the in vivo growth of transplantable, hormone-independent, and metastatic rat mammary carcinomas (DMBA-1, NMU-2) and LS-174T human colon carcinoma line

| Host | Tumor | Treatment | Total tumor no. | Change in mean tumor volume (cm$^3$) | (%) |
|---|---|---|---|---|---|
| rat | transpl. DMBA-1 | none | 15 | 2.63 | 100 |
|  |  | 8-Cl | 15 | 1.60 | 61 |
|  |  | DB | 15 | 2.60 | 99 |
|  | metastatic NMU-2 | none | 15 | 2.14 | 100 |
|  |  | 8-Cl | 15 | 1.10 | 51 |
|  |  | DB | 15 | 2.15 | 100 |
| nude mouse | LS-174T | none | 10 | 0.97 | 100 |
|  |  | 8-Cl | 10 | 0.58 | 60 |

DMBA-1, a variant of primary hormone-dependent DMBA tumor, hormone-independent and transplantable.
NMU-2, a variant of primary hormone-responsive NMU tumor, hormone-independent, transplantable, and metastatic.
LS-174T, human colon cancer line was s.c. grown in nude mice and a solid tumor, transplantable, was obtained.
8-Cl-cAMP and DB-cAMP were given as a 20-mg pellet consisting of 10 mg of cAMP analogue and 10 mg. cholesterol on day 0, and change in tumor volume was measured on day 7.

TABLE 6

Influence of 8-Cl-cAMP-Na$^+$ on the life span of non-tumor BDF$_1$ mice when delivered i.p. by bolus injection

| Dosage mg/kg/inj | Route and schedule of delivery | Toxic deaths No. killed/No. treated |
|---|---|---|
| 480 | ip; qd, day 1 | 5/5 |
| 288 | ip; qd, day 1 | 5/5 |
| 173 | ip; qd, day 1 | 2/5 |
| 104 | ip; qd, day 1 | 0 |
| 62 | ip; qd, day 1 | 0 |
| 37 | ip; qd, day 1 | 0 |
| 22 | ip; qd, day 1 | 0 |

When delivered qd, day 1 to non-tumor BDF$_1$ mice, the 480 and 288 mg/kg dosages of 8-Cl-cAMP-Na$^+$ were lethally toxic for all treated mice. The 173 mg/kg dosage killed 2 of 5 mice and lower dosages were not lethally toxic.

TABLE 7

Influence of 8-Cl-cAMP-Na$^+$ on the postinoculation lifespan of L1210-inoculated BDF$_1$ mice when infused or delivered by bolus injection

| Dosage (mg/kg/day) | Route and schedule of delivery | Postinoculation lifespan (T/C) |  |
|---|---|---|---|
| 104 | ip; qd, day 1–7 | 98 |  |
| 62 | ip; qd, day 1–7 | 103 |  |
| 37 | ip; qd, day 1–7 | 93 |  |
| 22 | ip; qd, day 1–7 | 103 |  |
| 800 | ip; 24-hr infusion, day 1–5 | 62 | toxic |
| 480 | ip; 24-hr infusion, day 1–5 | 93 | toxic |
| 288 | ip; 24-hr infusion, day 1–5 | 128 | toxic |
| 173 | ip; 24-hr infusion, day 1–5 | 131 |  |
| 104 | ip; 24-hr infusion, day 1–5 | 137 |  |
| 62 | ip; 24-hr infusion, day 1–5 | 137 |  |
| 37 | ip; 24-hr infusion, day 1–5 | 126 |  |
| 22 | ip; 24-hr infusion, day 1–5 | 126 |  |
| 13 | ip; 24-hr infusion, day 1–5 | 113 |  |
| 4.8 | ip; 24-hr infusion, day 1–5 | 100 |  |

TABLE 7-continued

Influence of 8-Cl-cAMP-Na⁺ on the postinoculation lifespan of L1210-inoculated BDF₁ mice when infused or delivered by bolus injection

| Dosage (mg/kg/day) | Route and schedule of delivery | Postinoculation lifespan (T/C) |
|---|---|---|
| 1.7 | ip; 24-hr infusion, day 1–5 | 100 |
| 0.6 | ip; 24-hr infusion, day 1–5 | 100 |

Mice were inoculated i.p. with 1 × 10⁶ cells of murine leukemia L1210 24-hr before first treatment. Each treatment group consisted of 5 mice. Twenty control mice that received a 0.9% solution of NaCl lived 6.2 ± 0.6 days. When infused, the 800 and 480 mg/kg dosages of 8-Cl-cAMP-Na⁺ were lethally toxic for all treated mice while the 288 mg/kg dosage killed 2 to 5 mice.
Infusions by Harvard pumps.
Single ip dose LD50 ~ 195 mg/kg
LD10 ~ 122 mg/kg

TABLE 8

Effects of 8-Cl-cAMP-Na⁺ on the Growth of Human Mammary Tumor Xenografts

| Xenograft | Ip infusion (mg/kg/day) for 7 days | Initial Mean Tumor Wt (mg)* | Final Mean Tumor Wt (mg)$ | % ΔT/T** or % ΔT/ΔC$$ |
|---|---|---|---|---|
| MX-1 mammary | control | 334 | 549 | |
| carcinoma | 173 | 375 | 336 | −10 |
| | 104 | 346 | 323 | −07 |
| | 62 | 337 | 288 | −15 |
| MDA-MB-231 | control | 361 | 726 | |
| mammary | 104 | 367 | 433 | +18 |
| carcinoma | 62 | 375 | 471 | +26 |
| | 37 | 367 | 516 | +41 |

*Mean tumor weight per group on staging day.
$Mean tumor weight per group on staging day +7.
**Change in *test tumor wt (final-initial)/initial test tumor wt. Used where test tumor size was reduced during treatment. Denoted by negative value.
$$Change in test tumor wt/change in control tumor wt. Used where test tumor size increased during treatment. Denoted by positive value.

TABLE 9

Effects of B-Cl-cAMP-Na⁺ on the Growth of Human Colon and Lung Tumor Xenograft

| Xenograft | Ip infusion (mg/kg/day) for 7 days | Initial Mean Tumor Wt (mg)* | Final Mean Tumor Wt (mg)$ | % ΔT/T** or % ΔT/ΔC$$ |
|---|---|---|---|---|
| LOVO Colon | Control | 292 | 376 | |
| carcinoma | 104 | 288 | 317 | −35 |
| | 62 | 293 | 290 | −01 |
| | 37 | 288 | 284 | −01 |
| LX-1-Lung | Control | 332 | 515 | |
| carcinoma | 104 | 324 | 270 | −17 |
| | 62 | 327 | 277 | −15 |
| | 37 | 330 | 341 | +06 |

*Mean tumor weight per group on staging day.
$Mean tumor weight per group on staging day +7.
**Change in test tumor wt (final - initial)/initial test tumor wt. Used where tumor size was reduced during treatment. Denoted by negative value.
$$Change in test tumor wt/change in control tumor wt. Used where test tumor size increased during treatment. Denoted by positive value.

It can be seen from the above that the site-selective analogues of cAMP are effective in arresting tumor growth at micromolar concentrations. The site-selective analogues, which are known to be many fold more active in their binding to the cAMP receptor protein, and, therefore, in cAMP-dependent protein kinase activation than the early known analogues in vitro, demonstrated their effectiveness at manyfold lower concentrations. Thus, cAMP-dependent protein kinase may be directly involved in the growth inhibition produced by the site-selective analogues tested here.

Table 10 shows the densitometric tracings of the autoradiograms at $A_{560}$ nm. The levels of the receptor proteins are expressed relative to the $R^I$ level in the untreated control cells of MDA-MB-231 and LS-174T, which are each set equal to 1.0 O.D.; the scale was expanded to differentiate the lower intensity bands.

TABLE 10

| | | RELATIVE LEVELS OF cAMP RECEPTOR PROTEINS | | | |
|---|---|---|---|---|---|
| CELL LINE | LANE | $R^I$ | $R^{II}$ | $\frac{R^{II}}{R^I}$ | % GROWTH |
| MDA-MB-231 | 1, 8-Cl | 0.25 ± 0.03 | 0.15 ± 0.01 | 0.60 | 45 |
| | 2, N⁶-BENZYL | 0.25 ± 0.03 | 0.07 ± 0.01 | 0.28 | 55 |
| | 3, DIBUTYRYL | 1.0 ± 0.1 | 0.07 ± 0.01 | 0.07 | 100 |
| | 4, CONTROL | 1.0 ± 0.1 | 0.05 ± 0.01 | 0.05 | 100 |
| LS-174T | 1, 8-Cl | 0.20 ± 0.02 | 0.25 ± 0.02 | 1.25 | 30 |
| | 2, N⁶-BENZYL | 0.20 ± 0.02 | 0.25 ± 0.02 | 1.25 | 35 |
| | 3, DIBUTYRYL | 0.80 ± 0.10 | 0.15 ± 0.02 | 0.19 | 85 |
| | 4, CONTROL | 1.0 ± 0.10 | 0.10 ± 0.02 | 0.10 | 100 |

TABLE 11

| Lane | p21 (Relative Level) | % Growth |
| --- | --- | --- |
| 1, Control | 1.0 ± 0.1 | 100 |
| 2, 8-Cl-cAMP (10 μM) | 0.1 ± 0.01 | 43 |
| 3, 8-Cl-adenosine (5 μM) | 1.0 ± 0.1 | 38 |
| 4, DBcAMP (500 μM) | 0.8 ± 0.1 | 80 |

Table 11 shows the densitometric tracings of autoradiograms at $A_{560}$ nm. The levels of p21 protein are expressed relative to the p21 level in the untreated control cells, which is set equal to 1.0 O.D.

The current approach to treating leukemia is to promote cell differentiation rather than cell killing. The site-selective cAMP analogues of the present invention, which are manyfold more active in protein kinase activation than the previously studied cAMP analogues, exert a major growth regulatory effect on a spectrum of human leukemic cell lines.

For the experiments described below, the leukemic cell lines used were HL-60 (acute promyelocytic), K-562 (chronic myelocytic), myc-K562 (chronic myelocytic), and Molt-4 (acute T lymphocytic).

The cells were grown in suspension culture in RPMI 1640 medium supplemented with 10% fetal bovine serum, penicillin (50 U/ml), streptomycin (500 microg/mL), 10 mmol/L HEPES buffer, and extra glutamine. For cell growth experiments, cells were treated with cAMP analogues one time at three hours after seeding, and cell counts in duplicate were performed on a Coulter counter 48 and 72 hours later. Surface antigen analysis of HL-60 cells was performed by flow cytometry using a panel of monoclonal antibodies reactive with either myeloid cells or monocytic cells. Terminal deoxynucleotidyl transferase (TdT) was assayed by an immunoperoxidase method using a TdT fluorescence kit. Western blotting of c-myc protein was performed using c-myc antibody 15206D11 (Scripps Clinic and Research Foundation, LaJolla, Calif.).

A variety of cAMP analogues, modified at either the C-6 or C-8 positions of the adenine moiety at various concentrations, were tested for their growth inhibitory effect on leukemic cell lines, as shown in Table 11. Among the C-8 analogues (site 1-selective) tested, 8-Cl-cAMP exhibited the most potency, demonstrating 50% growth inhibition at 5–20 micromol/L concentrations ($IC_{50}$) in all four leukemic cell lines. 8-Br-, 8-methylthio, and 8-methylamino-cAMP were 5 to 20 times less potent than 8-Cl-cAMP. $N^6$-benzyl-cAMP was the most potent of the C-6 analogues (site 2-selective) tested with $IC_{50}$ values of 10 to 30 micromol/L. $N^6$-benzoyl-cAMP, which is structurally similar to $N^6$-benzyl-cAMP, exhibited $IC_{50}$ values of 40 to 50 micromol/L. DBcAMP, the analogue most commonly used in previous studies, exhibited the least potency, the $IC_{50}$ values of 500 to 1000 micromol/L, and in Molt-4, the 50% growth inhibition could not be obtained. Growth inhibition by the site-selective cAMP analogues was not due to cell killing; the cells were 80% to 90% viable as determined by exclusion of trypan blue dye.

TABLE 12

Effect of Site-Selective cAMP Analogs on Growth of Leukemic Cell Lines

| Cyclic Nucleotide Analog | cAMP Analog | Inhibition of Growth $IC_{50}$ (μmol/L) | | | |
| --- | --- | --- | --- | --- | --- |
| | | HL-60 | Molt-4 | K-562 | myc-K562 |
| C-8 | 8-Chloro | 100 | 5 | 20 | 20 |
| | 8-Bromo | 50 | 100 | 100 | 100 |
| | 8-Thiomethyl | 100 | 100 | 100 | 100 |
| | 8-Aminomethyl | 100 | 100 | 100 | 100 |
| C-6 | $N^6$-Benzyl | 20 | 10 | 27 | 30 |
| | $N^6$-Benzoyl | 50 | 40 | 45 | 50 |
| | $N^6,O^{2'}$-Dibutyryl | 500 | —* | 1,000 | 1,000 |

*No growth inhibition.

Phosphodiesterase inhibitor, such as theophylline (0.1 mmol/L) or 1-methyl-3-isobutylxanthine (0.5 mmol/L), each alone had little or no growth inhibitory effect, and the inhibitors could not enhance the analog effect when added in combination with the analogue. These results suggest that the analogues produced growth inhibition at concentrations below which the degradation by phosphodiesterase could take places and also that the growth inhibition was not due to raising cellular cAMP.

The effect of site-selective cAMP analogues on the expression of differentiation markers in HL-60 cells was examined to determine if the growth-arrested HL-60 cells were more differentiated than the untreated cells. Treatment for three days with 8-Cl-cAMP exhibiting 90% viability induced a marked increase in the expression of monocyte-specific surface antigens ($MO_2$, $OKM_5$) and a decrease in markers related to the immature progenitor cells (My7, My9), cf. Table 13.

TABLE 13

Modulation of Differentiation Markers in HL-60 Cells by 8-Cl-cAMP

| Markers | Control % Positive | 8-Cl-cAMP* (20 μmol/L) % Positive |
| --- | --- | --- |
| My7 | 81 | 11 |
| My9 | 75 | 54 |
| Leu M1 | 72 | 0 |
| Leu M5 | 0 | 0 |
| $MO_2$ | 0 | 75 |
| $OKM_5$ | 0 | 51 |

*Seventy percent growth inhibition with 90% cell viability.

Disappearance of cellular TdT has been considered as a differentiation marker for human T lymphocytic leukemia. Treatment of Molt-4 (acute T lymphocytic) leukemia cells with 8-Cl-cAMP (10 micromol/L) caused a time-dependent decrease in TdT activity; at two days after the treatment, TdT activity decreased to 50% of that in untreated control cells, and by day 4, the activity decreased to 10% of the untreated control levels. Moreover, treatment for four days with 8-Cl-cAMP in combination with $N^6$-benzyl cAMP (20 micromol/L) caused almost complete loss (>95%) of TdT activity. These cells exhibiting the loss of TdT demonstrated >90% viability.

A propidium iodide staining method was used to determine if the reason for reduced cell proliferation observed in the leukemic cell lines after treatment with the analogues was due to a specific block in one phase of the cell cycle. The results showed that the fractions of cells in each phase of the cell cycle were not appreciably different between the control cells and the cells treated with the analogues.

The type I isozyme of cAMP-dependent protein kinase has been considered to be involved in cell proliferation and transformation, whereas the type II isozyme is involved in cell differentiation and inhibition of cell growth. Because type I and type II protein kinase differ only in their regulatory subunits, the cAMP binding receptor protein, the cAMP receptor protein was measured during the analogue treatment of these leukemic cells, using the photoaffinity ligand 8-$N_3$-[$^{32}$P]cAMP. As shown in FIG. 9,A, the untreated Molt-4 leukemic cells contained a major cAMP receptor protein with a molecular weight of 48,000 (lane 1), the $R^I$ cAMP receptor protein (the regulatory subunit of type I protein kinase). When the cells were treated for three days with 8-Cl-cAMP (lane 2), the $R^I$ receptor protein markedly decreased, whereas the $R^I$ protein remained without appreciable change when the cells were treated with DBcAMP (lane 3). That the decrease of the $R^I$ receptor photoaffinity labelling found after 8-Cl-cAMP treatment could be due to the presence of bound 8-Cl-cAMP to the $R^I$ receptor is unlikely; 8-Cl-cAMP, like 8-piperidino-cAMP, selectively binds to site 1 of $R^{II}$ but binds to site 2 of $R^I$ receptor. Thus, 8-Cl-cAMP bound to site 2 of $R^I$ would synergistically enhance, instead of interfere with, the site 1-selective binding of 8-$N_3$-[$^{32}$P]cAMP.

Figures 9A, 9B:
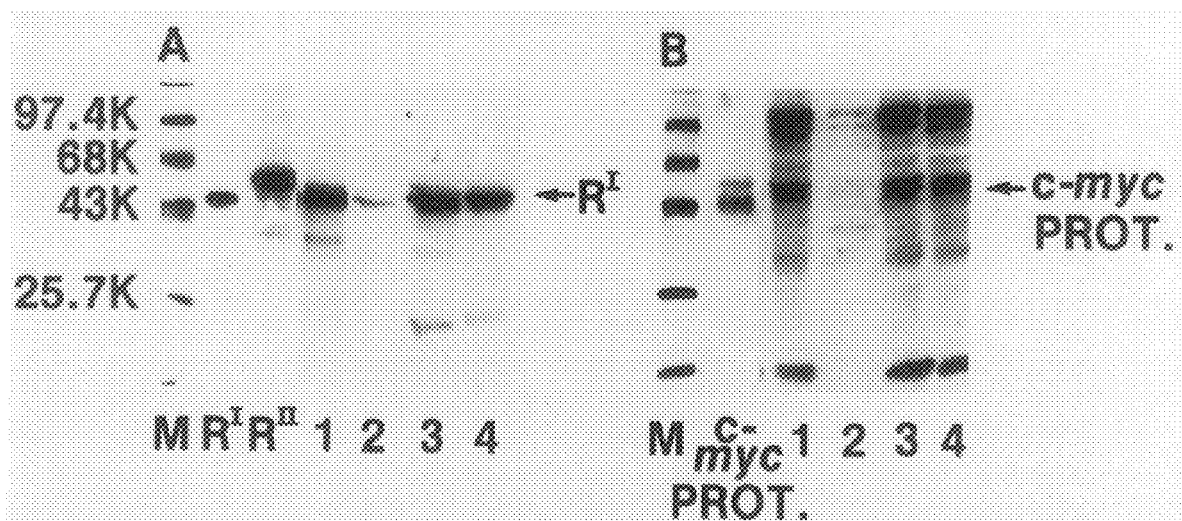

The 8-Cl-cAMP also caused a marked reduction of c-myc protein level, as shown in FIG. 9B, lane 2, whereas DBcAMP, lane 3, did not affect the c-myc protein level, indicating that a decrease in $R^I$ and c-myc protein levels caused by 8-Cl-cAMP treatment does not merely reflect growth inhibition or cell death in general. A similar decrease in RI and c-myc protein levels also occurred in other leukemic lines, K-562, myc-K562, and HL-60, after 8-Cl-cAMP treatment. The $R^{II}$ cAMP receptor protein was not detected in Molt-4, but was measurable in other leukemic cell lines. The analogue treatment did not affect the $R^{II}$ levels in these leukemic cells.

In FIG. 9, A shows the photoactivated incorporation of 8-$N_3$-[$^{32}$P]cAMP; B shows the Western blotting of c-myc protein; $R^{II}$, the 56,000 molecular weight $R^{II}$ cAMP receptor protein; c-myc proteins a purified preparation of c-myc protein. Lane 1, untreated control cells; and lanes 2 through 4, the cells treated for three days with 5 micromol/L of 8-Cl-cAMP, DBcAMP (1 mmol/L), and 8-Cl-adenosine (5 micromol/L), respectively. M marker proteins of known molecular weight. Each lane contained 100 micrograms protein for sodium dodecyl sulfate-polyacrylamide gel electrophoresis (SDS-PAGE). The cell pellets, after two washes with phosphate-buffered saline, were suspended in buffer ten (0.1 mol/L NaCl, 5 mmol/L $MgCl_2$, 1% Nonidet P-40, 0.5% Na deoxycholate, 2 KIU/mL bovine aprotinin, 20 mmol/L Tris-HCl, pH 7.4) ($2 \times 10^7$ cells/mL) vortexed, passed through a 22-gauge needle ten times, allowed to stand for 30 minutes at 4° C., and centrifuged at 750×g for 20 minutes at 4° C. The resulting supernatants were used as cell lysates. The numbers in the panel represent the average value±SE of seven separate experiments. ND=nondetectable.

As described above, the cAMP analogues of the present invention were shown to exert a major effect on the growth of promyelocytic, chronic myelocytic, and acute T lymphocytic human Leukemic cell lines at micromolar concentrations. The analogue effect was not due to raising of cellular cAMP levels as was previously believed, because phosphodiesterase inhibitors in combinations with the analogue did not enhance the analogue effect. The analogues worked directly through cAMP receptor proteins the regulatory subunit of cAMP-dependent protein kinase. Among the site-selective analogues tested, 8-Cl-cAMP exhibited the most potency. The analogue effect correlated with a selective modulation of two types of cAMP receptor proteins—a marked reduction in the $R^I$ receptor, which was previously related to cell growth and transformation, with no change in the $R^{II}$ receptor, which was related to growth arrest and differentiation.

This selective modulation of the $R^I$ and the $R^{II}$ cAMP receptor protein was not achieved by the early-known analogue, DBcAMP. The growth inhibition also caused a marked reduction in c-myc protein level. The decrease in the $R^I$ cAMP receptor and c-myc protein level was not observed when cells were growth-arrested by 8-Cl-adenosine, indicating that the analog effect was not due to its adenosine metabolite.

The growth arrest by the analogues accompanied differentiation of the leukemic cells, as shown by the expression of several surface antigens specific for monocytic differentiation in HL-60 cells and a loss of the activity of TdT, a marker enzyme for cell immaturity in Molt-4 cells. Despite the appearance of markers of mature phenotype and definitive growth arrest shown in the analogue-treated cells, the cell cycle phase distribution between the treated and untreated cells was similar.

In normal myeloid cell precursors, the growth inducers induce cell viability and cell multiplication and also production of differentiation inducers. In leukemic cells, therefore, continuous production of growth inducers may be essential for continuous production of differentiation inducers to achieve their terminal differentiation. The site-selective cAMP analogues, which produce growth arrest while allowing the cells to progress through their normal cell cycle but at a slower rate, may terminally differentiate leukemic cells because these agents allow continuous production of differentiation inducers. Thus, the site-selective cAMP analogues of the present invention restore the balance between proliferation and maturation of leukemic cells.

It has been shown also that the synergism of growth inhibition by C-6 analogues, when combined with 8-thio or 8-halogen analogues, far exceeds that by C6 analogues in combinations with 8-amino derivatives This suggests a response of type II rather than type I protein kinase. In fact, an increase in the $R^{II}$ cAMP receptor protein with a decrease in the $R^I$ receptor protein observed during growth inhibition correlated with the growth inhibitory potency of the analogues, cf. FIG. 5 and 6. This unique behavior of the site-selective analogues demonstrating selective modulation of the $R^I$ and $R^{II}$ cAMP receptor proteins in cancer cells in not mimicked by earlier known analogues, cAMP itself, or agents that increase cellular cAMP levels. cAMP at high levels, having no site selectivity, activates both type I and type II protein kinase isozymes maximally and equally without discrimination.

Because the site-selective cAMP analogues in combination brought about a synergistic effect, the combination permitted the use of lower total analogue concentration to achieve the same growth inhibitory effect as would be obtained using a single analogue. Thus, the site-selective analogues in combination exerted the growth inhibition at concentrations at least one-tenth below the reported $IC_{50}$ for the low Km cAMP phosphodiesterase. At these low concentrations the analogues would not be metabolized to produce their toxic adenosine analogues. In fact, by HPLC analysis, 8-Cl-adenosine was not detected in the cell extracts or medium after treatment of cells for 48–72 hours with 8-Cl-cAMP at a concentration as high as 50 microM. A role for 8-Cl-adenosine toxicity in the inhibition of cell growth was further excluded by the experimentation that showed the different behavior between 8-Cl-cAMP and 8-Cl-adenosine in cell cycle effect, release from growth inhibition, and modulation of p21 ras protein. Thus, the growth inhibitory effect of the site-selective compounds described herein clearly differs from that in previous reports that have shown strong cytotoxicity lethal to the rat hepatoma cells using some of the amino-substituted C-8 analogues and cyclic nucleotides of purine analogues.

Growth inhibition by the compounds of the present invention accompanied biochemical and morphological changes but did not produce G1 arrest in the cancer cells tested. It appears, therefore, that the compounds of the present invention produce growth inhibition by slowing down the cell cycle progression and perhaps promoting cell differentiation. In fact, a role of site-selective cAMP analogues in promotion of differentiation has been shown in leukemic cell lines.

The site-selective analogues of the present invention were able to arrest the growth of cancer cells that are resistant to comparable levels of DBcAMP. Thus, the site-selective cAMP analogues of the present invention are useful as a biological tool in the growth control of a wide spectrum of cancer cells, including those previously found to be resistant to other cAMP analogues or to agents that increase intracellular cAMP.

The compounds of the present invention are administered in amounts such as to provide a concentration of from about 0.1 to about 100 microM in the serum of the patient. The compounds may be administered in a variety of ways, including via osmotic pump, pellet implantation, or other method that may provide a continuous supply of the compound.

The compounds of the present invention may be administered in effective amounts in a variety of ways contained in a pharmaceutically acceptable carrier. Compositions within the scope of the invention include compositions wherein the compounds are contained in an effective amount to achieve the intended purpose. Determination of the effective amounts is within the skill in the art.

In addition to the cAMP analogue or combination of cAMP analogues and pharmaceutically acceptable salts thereof of the present invention, the pharmaceutical compositions may contain suitable pharmaceutically acceptable carriers comprising excipients and auxiliaries which facilitate processing of the active compounds into preparations which can be used pharmaceutically. Preferably, the preparations, particularly those which can be administered orally and which can be used for the preferred type of administration, such as tablets, dragees, and capsules, and also preparations which can be administered rectally, such as suppositories, as well as suitable solutions for administration by injection or orally, contain from about 0.1 to 99 percent, preferably from about 25 to 85 percent by weight of active ingredient, together with the excipient.

The pharmaceutical compositions of the present invention are manufactured in a known manner, for example, by means of conventional mixing, granulating dragee-making, dissolving, or lyophilizing processes. Thus, pharmaceutical preparations for oral use can be obtained by combining the active compounds with solid excipients, optionally grinding a resulting mixture and processing the mixture of granules, after adding suitable auxiliaries, if desired or necessary, to obtain tablets or dragee cores.

Suitable excipients are, in particular, fillers such as sugars, for example, lactose, sucrose, mannitol, or sorbitol; cellulose preparations; and/or calcium phosphates, such as tricalcium phosphate or calcium hydrogen phosphate, as well as binders, such as starch paste, using, for example, rice starch, corn starch, wheat starch, or potato starch; gelatin, gum tragacanth, methyl cellulose, hydroxypropylcellulose, sodium carboxymethylcellulose, and/or polyvinylpyrrolidone. If desired, disintegrating agents may be added, such as the above-mentioned starches and carboxymethyl starch, crosslinked polyvinyl pyrrolidone, agar, or alginic acid or a salt thereof, such as sodium alginate.

Auxiliaries include, above all, flow-regulating agents and lubricants, such as silica gel, talc, stearic acid, and salts thereof, such as magnesium stearate or calcium stearate, and/or polyethylene glycol. Dragee cores are provided with suitable coatings which, if desired, may be resistant to gastric juices. For this purpose, concentrated sugar solutions may be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as acetyl-cellulose phthalate or hydroxypropylmethyl-cellulose phthalate, are used. Dyestuffs and pigments may be added to the tablets or dragee coatings, for example, for identification or in order to characterize different combinations of active compound doses.

Other pharmaceutical preparations, which can be used orally, include push-fit capsules made of gelatin, as well as soft, sealed capsules made of gelatin and a plasticizer, such as glycerol or sorbitol. The push-fit capsules can contain the active compounds in the form of granules, which may be mixed with fillers, such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition, stabilizers may be added.

Possible pharmaceutical preparations, which can be used rectally, include, for example, suppositories which consist of a combination of the active compound with a suppository base. Suitable suppository bases are, for example, natural or synthetic triglycerides, paraffin hydrocarbons, polyethylene glycols, or higher alkanols. In addition, it is also possible to use gelatin rectal capsules, which consist of a combination of the active compounds, with a base. Possible base materials include, for example, liquid triglycerides, polyethylene glycols, or paraffin hydrocarbons.

Suitable formulations for parenteral administration include aqueous solutions of the active compounds in water-soluble or -dispersible form. These water-soluble or water-dispersible forms may be as pharmaceutically acceptable salts of the analogues, such as sodium, potassium, calcium, magnesium, and like salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances, which increase the viscosity of the suspension, such as sodium carboxymethyl cellulose, sorbitol, and/or dextran. Optionally, the suspension may also contain stabilizers.

The active ingredients may also be administered as liposomes, pharmaceutical compositions in which the active ingredient is contained either dispersed or variously present in corpuscles consisting of aqueous concentric layers adherent to lipidic layers (hydrophobic). The drug may be present both in the aqueous layer and in the lipidic one (inside or outside), or, in any event, in the non-homogeneous system generally known as a liposomic suspension.

The hydrophobic layer, generally but not exclusively, comprises phospholipids, such as lecithin and sphingomycelin, steroids, such as cholesterol, more or less ionic surface-active substances, such as diacetylphosphate, stearylamine or phosphatidic acid, and/or other materials of a hydrophobic nature.

While the invention is described above in relation to certain specific embodiments, it will be understood that many variations are possible, and that alternative materials and reagents can be used without departing from the invention. In some cases such variations and substitutions may require some experimentation, but such will only involve routine testing.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications are intended to be comprehended within the meaning and range of equivalents of the disclosed embodiments. It is to be understood that the phraseology or terminology herein is for the purpose of description and not of limitation,

What is claimed is:

1. A method of inhibiting the neoplastic growth of cancer cells comprising contacting said cells with a neoplastic growth inhibiting-effective amount of a combination of two cAMP derivatives, wherein one of said two cAMP derivatives is selective for site 1 of a type II cAMP dependent protein kinase and wherein another one of said two cAMP derivatives is selective for site 2 of type I or type II cAMP dependent protein kinase.

2. A method of inhibiting the neoplastic growth of cancer cells comprising contacting said cells with a neoplastic growth inhibiting-effective amount of a combination of cAMP derivatives that are modified at the C-6, C-8, or C-6 and C-8 positions, wherein a first cAMP derivative is modified at the C-6 or C-6 and C-8 position a second cAMP derivative is modified at the C-8 or C-6 and C-8 position, with the proviso that both of said first and said second cAMP derivatives are not cAMP derivatives modified at the C-6 and C-8 position, and wherein said C-6 substitutions are selected from the group consisting of N-benzylamino, N-ethoxycarbamido, N-benzamido, N-phenylcarbamamido, N-butyramido, N-butylamino, N-phenylamino, and N,N-diethylamino, or N-piperidino, and wherein said C-8 substituent is selected from the group consisting of halogen, methylthio, p-chlorophenylthio, N-(β-hydroxylethyl)amino and N-methylamino, and pharmaceutically acceptable salts of said C-6, C-8 and C-6 and C-8 cAMP derivatives.

3. The method of claim 2, wherein said combination of cAMP derivatives is added in vivo.

4. The method of claim 3, wherein said cells are selected from the group consisting of leukemia, mammary carcinoma cells, colon carcinoma cells, and lung carcinoma cells.

5. The method of claim 2, wherein said growth inhibiting amount is sufficient to cause differentiation of said cells.

6. The method of claim 1, wherein said growth inhibiting amount is sufficient to cause differentiation of said cells.

7. The method of claim 4, wherein said growth inhibiting amount is sufficient to cause differentiation of said cells.

8. The method of claim 2, wherein said derivative modified at the C-8 or C-6 and C-8 position is modified at the C-8 position only.

9. The method of claim 8, wherein said derivative modified at the C-8 or C-6 and C-8 position is modified at the C-8 with chloro, methylthio, bromo, iodo, p-chlorophenylthio, β-hydroxyethylamino, methylamino, or N,N-dimethylamino.

10. The method of claim 9, wherein said derivative is modified at the C-8 position with chloro.

11. The method of claim 10, wherein said growth inhibiting amount is sufficient to cause differentiation of said cells.

12. The method of claim 2, wherein said derivative modified at the C-6 or C-6 and C-8 position is modified at the C-6 position only.

13. The method of claim 12, wherein said derivative is modified with $N^6$-benzyl, $N^6$-ethoxycarbonyl, $N^6$-benzoyl, $N^6$-phenylcarbamoyl, $N^6$-butyryl, or $N^6,O^{2'}$-dibutyryl substitution.

14. The method of claim 13, wherein said derivative is modified with $N^6$-benzyl.

15. The method of claim 2, wherein one of two said derivatives are modified with $N^6$-phenyl-8-p-chlorophenylthio, $N^6,N^6$-diethyl-8-p-chlorophenylthio, 6-(N-piperidino-8-p-chlorophenylthio, $N^6$-benzyl-8-benzylthio, or $N^6$-n-butyl-8-p-chlorophenylthio.

16. The method of claim 15, wherein said derivative is $N^6$-phenyl-8-p-chlorophenylthio cAMP or $N^6$-phenyl-8-chloro cAMP.

* * * * *